United States Patent [19]

Baguley et al.

[11] Patent Number: 5,696,131
[45] Date of Patent: Dec. 9, 1997

[54] TREATMENT OF CANCERS

[75] Inventors: Bruce Charles Baguley, Hillsborough; Graham John Atwell, Meadowbank; William Alexander Denny, Pakuranga; Graeme John Finlay, Torbay; Gordon William Rewcastle, Manurewa, all of New Zealand

[73] Assignee: Xenova Limited, Slough, England

[21] Appl. No.: 387,565

[22] Filed: Feb. 13, 1995

Related U.S. Application Data

[63] Continuation of Ser. No. 7,690, Jan. 22, 1993, abandoned.

[51] Int. Cl.$^6$ .................................................. A61K 31/165
[52] U.S. Cl. .................................................. 514/297
[58] Field of Search .................................................. 514/297

[56] References Cited

U.S. PATENT DOCUMENTS

| | | | |
|---|---|---|---|
| 4,021,551 | 5/1977 | Cullen et al. | 514/297 |
| 4,590,277 | 5/1986 | Atwell et al. | |
| 5,229,395 | 7/1993 | Watanabe et al. | 514/297 |

OTHER PUBLICATIONS

Argiropoulos G, Bates MRM, Cherubim R, Deady LW, Ganagka AM, Baguley BC and Denny WA. Cytotoxic and DNA-Binding Properties of Aminoalkyl Derivatives of di-and triazaphenanthrenes. Anti-Cancer Drug Design, 1992, 7:285–296.

Atwell GJ, Cain BF, Baguley BC, Finlay GJ, Denny WA. Potential antitumor agents. 43. Synthesis and biological activity of dibasic 9-aminoacridine-4-carboxamides, a new class of antitumour agent. J Med Chem., 1984, 27:1481–1485.

Atwell GJ, Rewcastle GW, Baguley BC, Denny WA. Potential antitumor agents. 50. In vivo solid tumor activity of derivatives of N-[2-(dimethylamino)ethyl] acridine-4-carboxamide. J Med Chem., 1987, 30:664–669.

Atwell GJ, Baguley BC, Denny WA. Potential antitumor agents. 55. 6-Phenylphenanthridine-4-carboxamides: a new class of DNA-intercalating antitumor agents. J Med Chem., 1988, 31:774–779.

Atwell GJ, Bos CD, Baguley, BC, Denny WA. Potential antitumor agents. 56. "Minimal" DNA-Intercalating ligands as antitumor drugs: phenylquinoline-8-carboxamides. J Med Chem., 1988, 31:1048–1052.

Atwell GJ, Baguley BC, Denny WA. Potential antitumor agents. 57. 2-Phenylquinoline-8-carboxamides as "minimal" DNA-intercalating antitumor agents with in vivo solid tumor activity. J Med Chem., 1989, 32:396–401.

Baguley BC. DNA intercalating anti-tumour agents. Anti-Cancer Drug Design, 1991, 6:1–35.

Baguley BC, Calveley SB, Crowe KK, Fray LM, O'Rourke SA, Smith GP. Comparison of the effects of flavone acetic acid, fostriecin, homoharringtonine and tumour necrosis factor α on colon 38 tumours in mice. Eur J Cancer Clin. Oncol., 1989, 25:263–269.

Baguley BC, Finlay GF, and Ching LM. Resistance mechanisms to topoisomerase poisons: the application of cell culture methods. Oncology Res., 1992, 4(7):267–274.

(List continued on next page.)

*Primary Examiner*—Jose G. Dees
*Assistant Examiner*—Jane C. Osweki
*Attorney, Agent, or Firm*—Nixon & Vanderhye P.C.

[57] ABSTRACT

A new treatment schedule for administration of N-[2-(dimethylamino)ethyl]acridine-4-carboxamide and other related carboxamide anticancer drugs in which the drug is administered in a divided-dose schedule comprising two or more administrations at frequent intervals, for example every hour. Schedules to produce cyclic peaks/troughs in plasma levels are mentioned. The compounds can be used for circumventing multidrug resistance in cancers and may, for example, be used in combination with other cytotoxic drugs, especially non-topo II inhibitors. Treatment of melanoma and advanced colon cancer is included.

13 Claims, 10 Drawing Sheets

OTHER PUBLICATIONS

Bailly C, Denny WA, Mellor LE, Wakelin LPG and Waring MJ. Sequence specificity of the binding of 9–aminoacridine– –and amsacrine–4–carboxamides to DNA studied by DNase I footprinting. Biochemistry, 1992, 31, 3514–3524.

Chen KX, Gresh N, and Pullman B. Groove Selectivity in the Interaction of 9–aminoacridine–4–carboxamide antitumor agents with DNA. FEBS Let., 1987, 224(2):361–364.

Cornford EM, Young D, Paxton JW. Comparison of the blood–brain barrier and liver pentration of acridine antitumor drugs. Cancer Chemother Pharmacol., 1992, 29: 439–444.

Denny WA. DNA–intercalating ligands as anti–cancer drugs: prospects for future design. Anti–Cancer Drug Design, 1989, 4: 241–263.

Denny WA. Acridine–based antitumour agents. In "The Chemistry of Antitumour Agents", (Ed. DEV Wilman). Blackie & Co., London 1990, pp. 1–29.

Denny WA, Atwell GJ, Rewcastle GW, Baguley BC. Potential antitumor agents. 49. 5–substituted derivatives of N–[2–(dimethylamino)ethyl]–9–aminoacridine–4–carboxamide with in vivo solid tumor activity. J Med Chem., 1987, 30:658–663.

Denny WA, Atwell GJ, Baguley BC. "Minimal" DNA–intercalating agent as antitumour drugs: 2–styrylquinoline analogues of amsacrine. Anti–Cancer Drug Design, 1987, 2:263–270.

Denny WA, Wakelin LPG. Tricyclic carboxamides: relationships between antitumor activity and the geometry and kinetics of binding to DNA. In, "Structure and Expression, vol. 2 DNA and its Drug Complexes" (Eds. RH Sarma and MH Sarma), Adenine Press, NY 1988, pp. 329–337.

Denny WA, Rewcastle GW, Baguley BC. Potential antitumor agents. 59. Structure–activity relationships for 2–phenylbenzimidazole–4–carboxamides, a new class of 'minimal' DNA–intercalating agents which may not act via topoisomerase II. J Med Chem., 1990, 33:814–819.

Denny WA, Turner PM, Atwell GJ, Rewcastle GW, and Ferguson LR. Structure activity relationships for the mutagenic activity of tricyclic intercalating agents in Salmonella typhimurium. Mutation Res., 1990, 232:233–241.

Denny WA. The role of medicinal chemistry in the discovery of DNA–active anticancer drugs: from random searching, through lead development, to de novo design. Chapter 2 in, "Cancer Biology and Medicine, vol. 3: The Search for New Anti–Cancer Drugs" (Eds. M.J. Waring and B. Ponder), Kluwer, London, pp. 19–54 (1992).

Denny WA, Roos IAG and Wakelin LPG. Interrelations between anti–tumour activity, DNA breakage and DNA binding kinetics for 9–aminoacridinecarboxamide antitumour agents. Anti–Cancer Drug Design, 1986, 1:141–147.

Evans SMH, Young D, Robertson IGC, Paxton JW. Intraperitoneal administration of the antitumour agent N–[2–(dimethylamino)ethyl]acridine–4–carboxamide in the mouse: bioavailability, pharmacokinetics and toxicity after a single dose. Cancer Chemother Pharmacol., 1992, 31:32–36.

Ferguson LR, Hill CM, Baguley BC. Genetic toxicology of tricyclic carboxamides, a new class of DNA binding antitumour agent. Eur J Cancer, 1990, 26(6):709–714.

Ferguson LR and Denny WA. Frameshift mutagenesis by acridines and other reversibly binding DNA ligands. Mutagenesis, 1990, 5(6):529–540.

Ferguson LR and Denny WA. The genetic toxicology of acridines. Mutation Res., 1991, 258:123–160.

Finlay GJ, Baguley BC. Selectivity of N–[2–(dimethylamino)]ethyl]acridine–4–carboxamide towards Lewis lung carcinoma and human tumour cell lines in vitro. Eur J Cancer Clin Oncol., 1989, 25:271–277.

Finlay GJ, Wilson WR, Baguley BC. Chemoprotection by 9–aminoacridine derivatives against the cytotoxicity of topoisomerase II–directed drugs. Eur J Cancer Clin Oncol., 1989, 25(12):1695–1701.

Finlay GF, Baguley BC. Potentiation by phenylbisbenzimidazoles of cytotoxicity of anti–cancer drugs directed against topoisomerase II. Eur J Cancer, 1990, 26(5):586–589.

Finlay GJ, Marshall E, Matthews JHL, Paull KD, Baguley BC. In vitro assessment of N–[2–(dimethylamino)ethyl] acridine–4–carboxamide, a DNA–intercalating antitumour drug with reduced sensitivity to multidrug resistance. Cancer Chemother Pharmacol., 1993, 31:401–406.

Haldane A, Finlay GJ, Gavin JB, Baguley BC. Unusual dynamics of killing of cultured Lewis lung cells by the DNA–intercalating antitumour agent N–[2–(dimethylamino)ethyl]acridine–4–carboxamide. Cancer Chemother Pharmacol., 1992, 29:475–479.

Hudson BD, Kuroda R, Denny WA, and Neidle S. Crystallographic and molecular mechanics calculations on the antitumor drugs N–[(2–dimethylamino)ethyl]–and N–[(2–dimethyl–amino)butyl]–9–aminoacridine–4–carboxamides and their dications: implicaitons for models of DNA binding. J Biomol Stuct Dynamics, 1987, 5(1):145–158.

Lee HH, Denny WA. An Improved Synthesis of Substituted Dibenzo[1,4]dioxines. J Chem Soc Perkin Trans 1, 1990, 1:1071–1074.

Lee HH, Palmer BD, Baguley BC, Chin M, McFadyen WD, Wickham G, Thorsbourne–Palmer D, Wakelin LPG and Denny WA. DNA–directed alkylating agents. 5. Acridinecarboxamide derivatives of (1,2–diaminoethane)dichloroplatinum(II). J Med Chem, 1992, 35:2983–2987.

Lee HH, Palmer BD, Boyd M, Baguley BC, Denny WA. Potential Antitumor Agents. 64. Synthesis and Antitumor Evaluation of Dibenzo[1,4]dioxin–1–carboxamides: A new class of weakly binding DNA–intercalating agents. J Med Chem., 1992, 35:258–266.

Marshall ES, Finlay GJ, Matthews JHL, Shaw JHF, Nixon J., Baguley BC. Microculture–based chemosensitivity testing: a feasibility study comparing freshly explanted human melanoma cells with human melanoma cell lines. J Natl Cancer Inst., 1992, 84:(5):340–345.

McKenna R, Beveridge A, Jenkins, TC, Neidle S, Denny WA. Molecular modelling of DNA–antitumour drug intercalation interactions: correlation of structural and energetic features with biological properties for a series of phenylquinoline–8–carboxamide compounds. Mol Pharmacol., 1989, 35: 720–728.

Moyer SR, and Jurs PC. A Structure–Activity Relationship for the Binding of acridine–4–carboxamides to DNA. Quantitative Structure–Activity Relationships, 1990, 9:333–339.

O'Connor CJ, Emery DP, Tank H, Denny WA and Sunamoto J. Lysis of egg phosphatidylcholine vesicles by tricyclic carboxamide antitumour agents. Chem Biol Int., 1990, 75:93–104.

Palmer BD, Boyd M, Denny WA. Aromatic lithiation directed by the carboxylic acid groups: Synthesis of 9–substituted dibenzodioxin–1–carboxylic acids and 6–substituted phenoxanthiin–4–carboxylic acids. J Org Chem., 1990, 55: 438–441.

Palmer BD, Rewcastle GW, Atwell GJ, Baguley BC, Denny WA. Potential antitumor agents. 54. Chromophore requirements for in vivo antitumor activity among the general class of linear tricyclic carboxamides, J Med Chem.,1988,31: 707–712.

Paxton JW, Young D, Evans SMH, Kestell P, Robertson IGC, Cornford EM. Pharmacokinetics and toxicity of the new antitumour agent N–[2–dimethylamino)ethyl] acridine–4–carboxamide after i.v. administration in the mouse. Cancer Chemother Pharmacol., 1992, 29:379–384.

Piestrzeniewica M, Czyz M, Denny WA and Gniazdowski M. Inhibition of RNA synthesis in vitro by 9–aminoacridine carboxamide antitumor agents. Effects on overall RNA synthesis and synthesis of the initiating dinucleotide. Acta. Biochim. Polonica, 37(2):299–307 (1990).

Rewcastle GW, Synthesis and development of two new classes of anticancer drugs: the tricyclic carboxamides and the xanthenoneacetic acids. Chemistry in New Zealand 1989,53:145–150.

Rewcastle GW, Atwell GJ, Chambers D, Baguley BC, Denny WA. Potential antitumor agents. 46. Structure–activity relationships for acridine monosubstituted derivatives of the antitumor agent N–[2–(dimethylamino)ethyl] –9–aminoacridine–4–carboxamide. J Med Chem., 1986, 29:472–477.

Rewcastle GW, Denny WA, Baguley BC, Potential antitumor agents. 51. Synthesis and antitumor activity of substituted phenazine–1–carboxamides. J Med Chem., 1987, 30:843–851.

Robertson IGC, Palmer BD, Officer M, Siegers DJ, Paxton JW, Whaw GJ. Cytosol mediated metabolism of the experimental antitumour agent acridine carboxamide to the 9–acridone derivative. Biochem Pharmacol., 1991,42(10):1879–1884.

Schneider E, Darkin SJ, Lqwson PA, Ching L–M, Ralph RK, Baguley BC. Cell line selectivity and DNA breakage properties of the antitumour agent N–[2–(dimethylamino)ehtyl]acridine–4–carboxamide: role of DNA topoisomerase II. Eur J Cancer Clin Oncol., 1988, 24(11):1783–1790.

Wakelin LPG, Atwell GJ, Rewcastle GW, Denny WA. Relationships between DNA binding kinetics and biological activity for the 9–aminoacridine–4–carboxamide class of antitumor agents. J Med Chem., 1987, 30:855–861.

Wakelin LPG, Chetcuti P, Denny WA. Kinetic and equilibrium binding studies of amsacrine–4–carboxmides: a class of asymmetrical DNA–intercalating agents which bind by threading through the DNA helix. J Med Chem., 1990, 33:2039–2044.

Wakelin, LPG and Denny, W.A. Kinetic and equilibrium binding studies of a series of intercalating agents that bind by threading a sidechain through the DNA helix. In. "Molecular Basis of Specificity in Nucleic Acid–Drug Interactions" (Eds. B. Pullman & J. Jortner), Kluwer Academic, pp.191–206 (1990).

Woynarowki J, McCarthy K, Reynolds B, Beerman T, and Denny W. Are second generation analogs of amsacrine (polycyclic carboxamides) targeted at topoisomerase II? Proc. Am. Assoc. Cancer Res., 1990, 31:438, (Abstract).

Young D, Evans PC, Paxton JW. Quantitation of the antitumour agent N–[2–(dimethylamino)–ethyl] acridine–4–carboxamide in plasma by high performance liquid chromatography. J. Chromatography, 1990, 528:385–394.

Baguley et al., 1990, Design of DNA Intercalators to Overcome Topoisomerase II–Mediated Multidrug Resistance, J National Cancer Inst 82(5):98–102.

Traganos et al, 1987, Effects of a New Amsacrine Derivative, N–5–Dimethyl–9–(2–methoxy–4–methylsulfonylamino) phenylamino–4–acridinecarboxamide, on Cultured Mammalian Cells, Cancer Res 47:424–432.

DELTA VALUES

DELTA VALUES

DELTA VALUES

DELTA VALUES

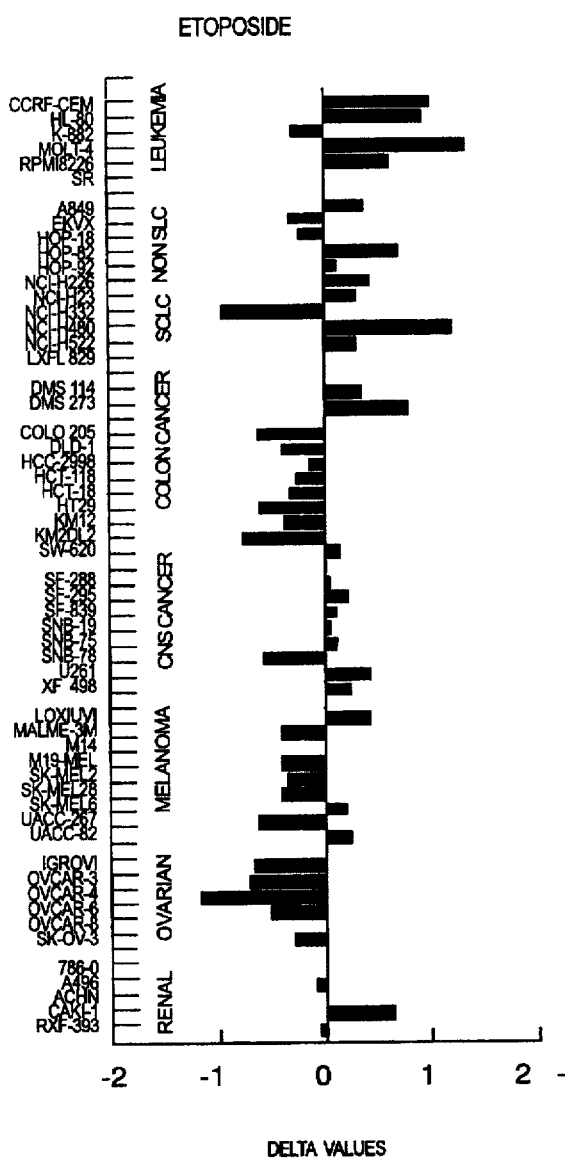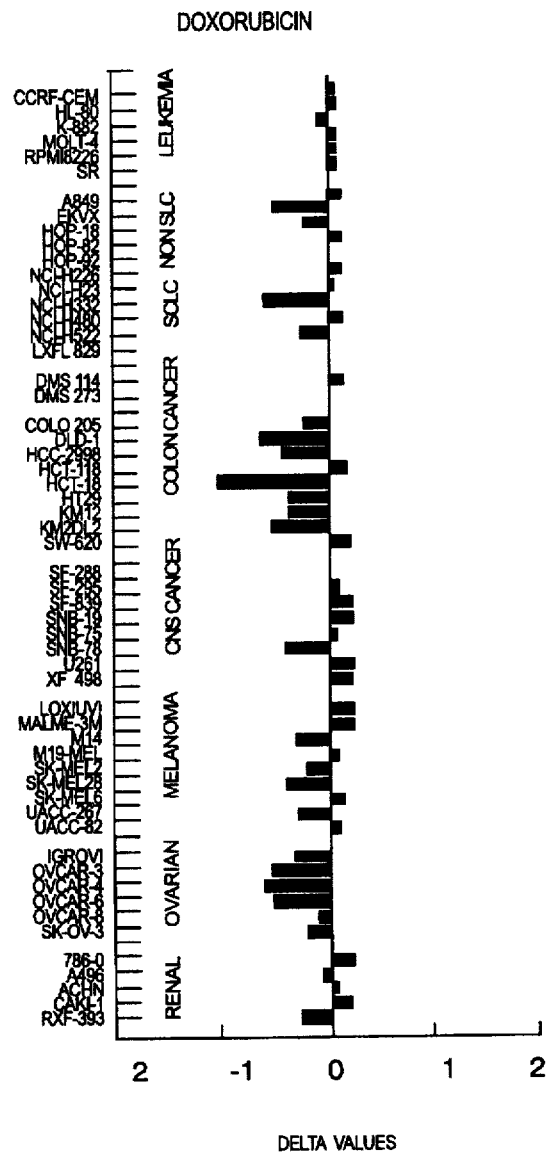
FIG. 3C
FIG. 3D

● = 4 injections i.p. at 30 minute intervals : 65 mg/kg, 45 mg/kg, 45 mg/kg, 45mg/kg; repeated after 7 days and at 14 days △ = single administration 150 mg/kg ○ = control

TREATMENT OF CANCERS

This is a Rule 60 continuation of application Ser. No. 08/007,690, filed Jan. 22, 1993, now abandoned.

The present invention relates to the treatment of tumours, especially to the treatment of melanoma and cancer of the colon, and to the circumvention of multidrug resistance in cancer treatments.

BACKGROUND OF THE INVENTION

For certain types of cancer, chemotherapy has been capable of rendering patients with responsive tumours free of disease. However, this responsive category does not include the most frequently encountered forms of malignant tumours.

The most common types of cancer in western populations are colon, lung and breast cancer. Each of these can be treated to some extent with existing chemotherapy, with different drugs being used preferentially for each type of malignancy (for instance, doxorubicin, cyclophosphamide and methotrexate for breast cancer, 5-fluorouracil for colon cancer), but response rates are not good. In addition, melanoma is a disease which is increasing in incidence at an alarming rate among fair-skinned populations. In melanoma, only 25-30% of patients with disseminated disease respond to treatment, and only 5-10% sustain durable remission (Evans B. D., et al., Proc. Am. Soc. Clin. Oncol. 1990, 9, 276).

There is therefore a great need for new types of cancer therapy, and a desperate need for such treatments for the above cancers in particular.

The basis for the development of the majority of anticancer drugs used today has been a panel of mouse tumours including transplantable leukaemias, the Lewis lung carcinoma and the colon 38 adenocarcinoma. A number of human tumour xenografts in mice have also been used. In general, the leukaemias are the most sensitive to experimental agents, the xenografts are the most resistant and the Lewis lung and colon 38 are of intermediate sensitivity (Goldin A., et al., Eur. J. Cancer 1981, 17, 129–142).

The murine Lewis lung adenocarcinoma is a tumour which initially arose spontaneously in $C_{57}Bl$ mice and which has a number of features which make it a good model for clinical carcinomas. It grows easily both in vitro and in vivo, and is aneuploid, heterogeneous, metastatic and resistant to many but not all clinical antitumour agents. Zacharski (Zacharski L. R., Haemostasis 1986, 16, 300–320) has concluded that although Lewis lung has the cytological appearance of a large-cell cancer, its rapid rate of growth, propensity to cause lethal metastases, as well as its susceptibility to combination chemotherapy, radiation and anticoagulant treatment, make it a good model for human small-cell lung cancer (SCLC). The colon 38 tumour arose in carcinogen-treated mice, and because it is sensitive to 5-fluorouracil it can be considered as a useful model for human colon cancer (Corbett T. H., et al., Cancer Chemother. Rep. 1975, 5, 169–186, and Cancer 1977, 40, 2660–2680). Human melanoma xenografts have been considered for some time as an appropriate model for the development of new anticancer drugs for melanoma (Taetle R., et al., Cancer 1987, 60, 1836–1841).

The essence of treating cancer with cytotoxic anticancer drugs is to combine a mechanism of cytotoxicity with a mechanism of selectivity for tumour cells over host cells. The selectivity of a drug for a particular cancer will depend on the expression by that cancer of properties which promote drug action, and which differ from tumour to tumour.

Currently available cytotoxic drugs can be broadly divided into four groups: those which react chemically with DNA (such as the alkylating agents and cisplatinum), those which disrupt DNA synthesis (such as the anti-metabolites), those which disrupt the mitotic apparatus (such as the Vinca alkaloids) and those which are directed against the cellular enzyme topoisomerase II ("topo II") in order to effect changes in the topological form of the DNA.

DNA topoisomerases were named after the first method used to detect their activity. When incubated with closed circles of double-stranded DNA prepared from viruses or bacteria, topoisomerases enzymatically change the number of coils contained in each circle (circular forms of DNA with different degrees of coiling are called topo-isomers). The topoisomerases are perhaps better understood as enzymes which temporarily break one strand of the DNA double helix (topoisomerase I or "topo I") or which simultaneously break two strands of the DNA double helix ("topo II") in order to effect changes in the topological form of the DNA.

Topoisomerases have two main functions in the cell. The first is to act as swivel points on the DNA in association with DNA and RNA polymerases during the biosynthesis of nucleic acids required for cell replication and gene expression. The second is to untangle the DNA strands of the daughter chromosomes following DNA replication prior to cell division. The DNA of chromosomes is organised as a series of loops on a protein-aceous "scaffold". After duplication of chromosomes and of the "scaffolds", the DNA loops must be separated. Since there are hundreds of thousands of DNA loops attached to each chromosome scaffold it is not hard to imagine the necessity for an enzyme which effectively removes tangles by passing one double DNA strand through another. This process absolutely requires topo II.

Topo I acts by transiently breaking a DNA strand and attaching itself to one of the free ends of the broken DNA via the amino acid tyrosine. Topo II contains two identical protein subunits, each of which is capable of breaking a DNA strand and attaching itself to one of the free ends. With both DNA strands broken, a second DNA double helix can be allowed to pass between the two enzyme protein subunits, thus allowing not only swivelling but also untangling of DNA. The process is normally spontaneously reversible by cleavage of the enzyme-DNA links and re-sealing of DNA breaks to restore the DNA to its original form.

Topo II-directed agents include a number of important clinical anti-cancer drugs such as anthracycline antibiotics (e.g. doxorubicin), epipodophyllotoxin derivatives (e.g. etoposide) and synthetic DNA intercalating drugs (e.g. amsacrine). These act by jamming the enzyme in its DNA-associated form (Liu L. F., Annu. Rev. Biochem. 1989, 58, 351–375). Such molecular lesions might be expected to be innocuous, since the drug eventually dissociates itself from the complex and the DNA strand breaks are then repaired perfectly. However, in a small proportion of cases, the presence of drug causes the complex to be dissociated abnormally, generating some kind of DNA lesion which eventually leads to cell death.

Although the antitumour activity of many of these agents has been known for many years, it is only since 1984 that the molecular target of action has been identified (Nelson E. M., Tewey K. M., Liu L. F., Proc. Natl. Acad. Sci. USA 1984, 81, 1361–1364 and Tewey K. M., et al., Science 1984, 226, 466–468).

A number of mechanisms of resistance to topo II poisons have now been identified, and in many cases the development of resistance to one drug is accompanied by the simultaneous acquisition of resistance to a variety of other drugs. Since the mechanism of resistance determines the pattern of cross-resistance to other drugs, an understanding of these processes is of great importance to the strategy for the use of these agents. Several resistance mechanisms important to the use of these agents have now been characterised in experimental systems, including those involved in drug transport (Endicott J. A., Ling V., Annu. Rev. Biochem 1989, 58, 351–375), drug-target interaction (Beck W. T., Biochem. Pharmacol. 1987, 36, 2879–2888) and drug detoxification (Deffie A. M., et al., Cancer Res. 1988, 48, 3595–3602).

Attempts to overcome multidrug resistance (mdr) clinically have been concerned mainly with the first of these mechanisms, a drug transport mechanism that pumps drug out of cells. Various inhibitors of this process, such as verapamil, are known and some have been used in combination with drugs such as doxorubicin and etoposide to treat cancer (Stewart D. J., Evans W. K., Cancer Treat. Rev. 1989, 16, 1–10, Judson I. R., Eur. J. Cancer 1992, 28, 285–289).

Another approach is to design drugs which can overcome mdr. We have now discovered that the investigational drug acridine carboxamide ("DACA") appears to be one such drug.

The compound tested was the dihydrochloride of N-[2-(dimethylamino)ethyl]acridine-4-carboxamide of formula

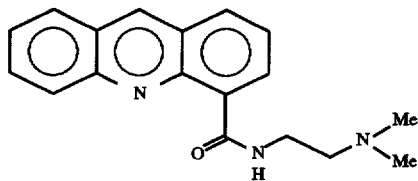

and is described and claimed in EP 98098. That patent also describes and claims other acridine carboxamide compounds and their use for the treatment of tumours; more particularly, the treatment of Lewis lung tumours and leukaemia is described.

Various other derivatives of DACA have been tested for their antitumour activity and the results are reported in the literature. Active, compounds are carboxamides having an unsubstituted or substituted aromatic ring system comprising two or more fused rings and having an oxygen or an aromatic nitrogen peri to the carboxamide side chain. As well as the other acridine carboxamides (EP 98098 and Denny W. A., et al., J. Med. Chem. 1987; 30: 658–663), examples are phenyl quinoline and pyrido quinoline carboxamides (EP 206802 A, Atwell G. J., et al., J. Med. Chem. 1988; 31: 1048–1052 and Atwell G. J., et al., J. Med. Chem. 1989; 32: 396–401), phenazine carboxamides (EP 172744 A and Rewcastle G. W., et al., J. Med. Chem. 1987; 30: 843–851), carboxamides having angular tricyclic chromophores: phenanthridine carboxamides (NZ Patent 215286, 1986 and Atwell G. J., et al., J. Med. Chem. 1988; 31: 774–779) and carboxamides having various linear tricyclic chromophores (Palmer B. D., et al., J. Med. Chem. 1988; 31: 707–712). These other compounds are structurally very similar to DACA and are able to act in the same way.

DACA is a DNA-binding drug which acts at the same target, topoisomerase II, as do drugs such as amsacrine and etoposide. We have now found that it has a different in vitro cytotoxicity profile to these compounds and a number of advantages over existing clinical drugs in the class of topoisomerase-directed agents.

Firstly, it is active against cell lines displaying both P-glycoprotein-mediated or "transport" resistance and "atypical" or "altered" multidrug resistance; in this respect it is unique among topo II inhibitors.

DACA and related compounds may therefore be used to circumvent mdr. For this it may be used in combination with other cytotoxic drugs, more especially non-topo II inhibitors, and/or as a second-line treatment if first-line treatment fails because of the development of multidrug resistance.

BRIEF DESCRIPTION OF THE DRAWINGS

The invention is further explained with reference to the attached drawing in which.

DESCRIPTION OF THE INVENTION

Figure 1A:
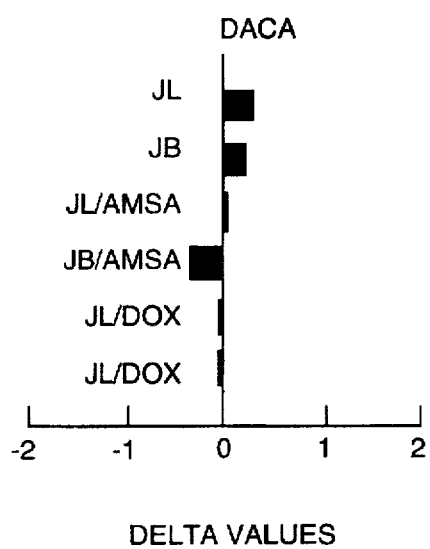
FIG. 1 is a graph showing comparisons of DELTA values in log mean graph format for DACA, amsacrine, etoposide, doxorubicin, vincristine, 5-fluorouracil, camptothecin and mitozantrone.
Figure 1B:
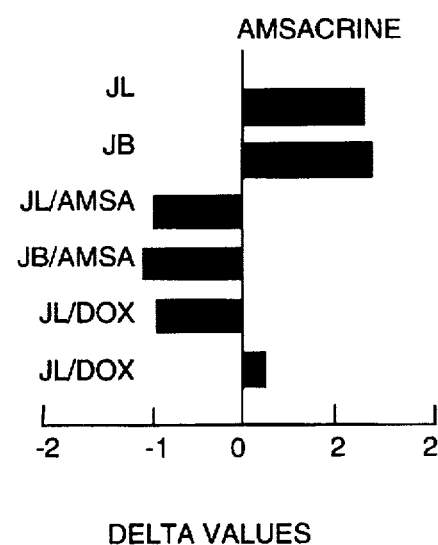
Figure 1C:
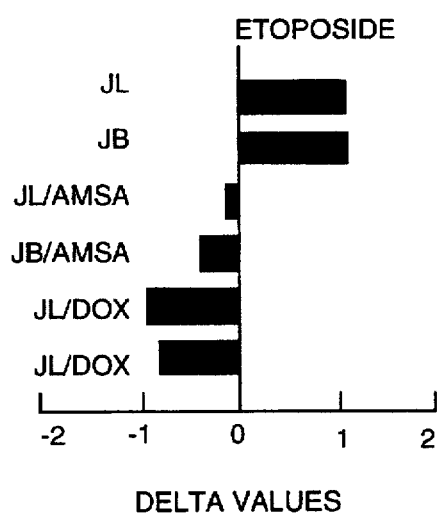
Figure 1D:
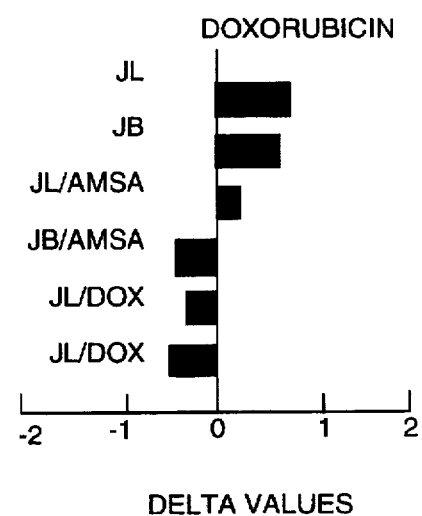
Figure 1E:
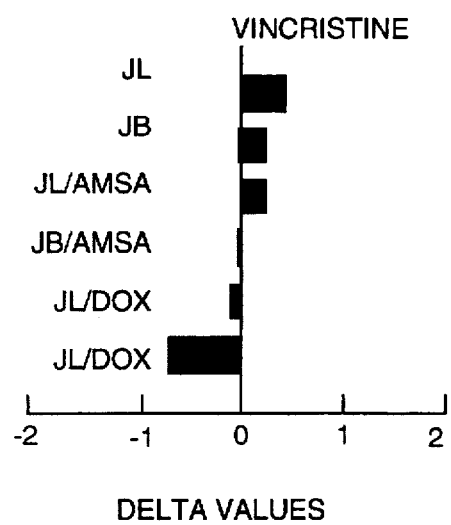
Figure 1F:
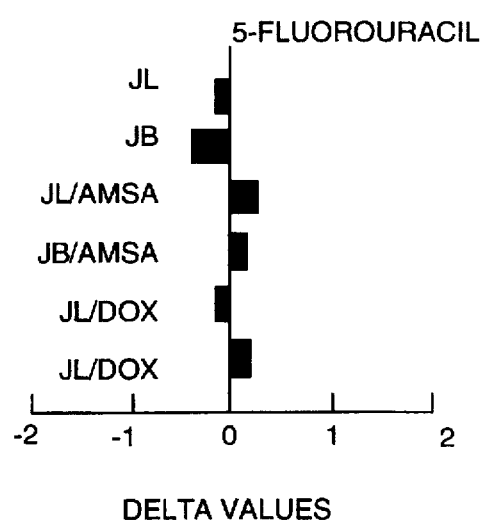
Figure 1G:
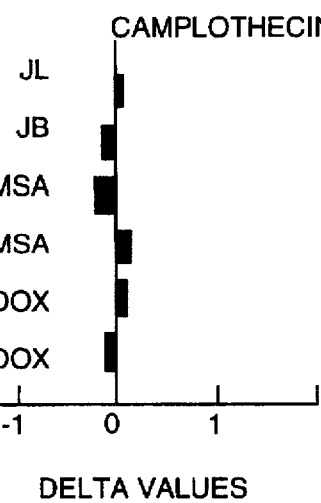
Figure 1H:
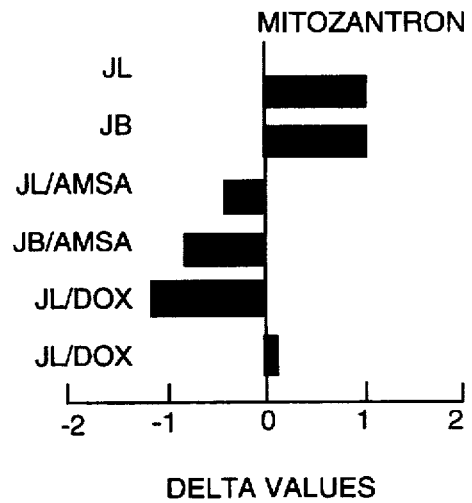

Accordingly, the present invention provides the use of DACA or other aromatic fused-ring carboxamide having an aromatic nitrogen atom or an oxygen atom peri to the carboxamide side chain or a physiologically tolerable acid addition salt thereof, for the manufacture of a medicament for overcoming mdr.

The present invention further provides a method of overcoming mdr, wherein there is administered DACA or other aromatic fused-ring carboxamide having an aromatic nitrogen atom or an oxygen atom peri to the carboxamide side chain or a physiologically tolerable acid addition salt thereof.

The present invention further provides a pharmaceutical preparation comprising (i) DACA or other aromatic fused-ring carboxamide having an aromatic nitrogen atom or an oxygen atom peri to the carboxamide side chain or a physiologically tolerable acid addition salt thereof, and (ii) a DNA-reactive agent, a DNA-synthesis inhibitor or an agent which disrupts the mitotic apparatus, in admixture or conjunction with a pharmaceutically suitable carrier.

The present invention also provides a combined preparation for use in the treatment of cancer, comprising separate components (i) and (ii) above for simultaneous or sequential administration.

Secondly, we have found that, unexpectedly, DACA is effective against advanced colon 38 tumours and an advanced melanoma xenograft in mice colon when administered in a divided dose schedule over a period of two hours. (In this context "advanced tumour" means that the tumour was more than 5 mm in diameter at the time of measurement.) In contrast, a single administration of DACA at the maximum tolerated dose (150 mg/kg), which is curative against Lewis lung tumours growing as lung nodules in mice, was only marginally effective.

Thirdly, DACA has the ability to cross the blood brain barrier, suggesting that rapidly growing brain tumours may also be treatable, more especially when administered in a divided dose schedule.

Accordingly, the present invention provides the use of DACA or other aromatic fused-ring carboxamide having an aromatic nitrogen atom or an oxygen atom peri to the carboxamide side chain or a physiologically tolerable acid addition salt thereof, for the manufacture of a medicament for the treatment of detectable colon cancer, melanoma or brain tumours, more especially by administration of a divided dose, the constituent doses being administered at frequent intervals.

The present invention further provides a method for the treatment of detectable colon cancer, melanoma or brain tumours, wherein there is administered DACA or other aromatic fused-ring carboxamide having an aromatic nitrogen atom or an oxygen atom peri to the carboxamide side chain or a physiologically tolerable acid addition salt thereof, more especially by administration of a divided dose, the oenstituent doses being administered at frequent intervals.

There may, for example, be at least 2 administrations in total in the divided dose, administrations being at least every 2 hours, for example every hour or every ½ hour, for up to 4 hours.

Thus, the present invention also provides the use of DACA or other aromatic fused-ring carboxamide having an aromatic nitrogen atom or an oxygen atom peri to the carboxamide side chain or a physiologically tolerable acid addition salt thereof, for the manufacture of a divided-dose medicament for the treatment of tumours, including melanoma and colon and brain tumours, by a treatment regime comprising 2 to 4 administrations of drug over a period of up to 4 hours, for example 2 to 4 hours.

The present invention also provides a method for the treatment of tumours, including melanoma and colon tumours, which comprises the administration of a divided dose of DACA or other aromatic fused-ring carboxamide having an aromatic nitrogen atom or an oxygen atom peri to the carboxamide side chain or a physiologically tolerable acid addition salt thereof, 2 to 4 constituent doses being administered over a period of up to 4 hours, for example 2 to 4 hours.

Fourthly, we believe that suitable DNA-binding compounds will reduce the toxicity of DACA when administered in conjunction with a divided high-dose schedule of DACA. DNA-binding compounds include, for example 9-aminoacridine; such compounds have the ability to inhibit the antitumour activity of DACA.

Accordingly, the present invention provides the use of a DNA-binding agent in combination with DACA or other aromatic fused-ring carboxamide having an aromatic nitrogen atom or an oxygen atom peri to the carboxamide side chain or a physiologically tolerable acid addition salt thereof, to reduce the host toxicity of DACA or specified other compound.

Doses in mice of 100 to 300 mg/kg, especially 150 to 250 mg/kg, more especially substantially 200 mg/kg, administered as a divided dose over a period of 2 to 4 hours, have proved suitable. Administration to humans of, for example, substantially 800 mg/m$^2$ of DACA or equivalent amount of other carboxamide, should be mentioned, but lower or higher amounts may also be possible. As explained above, advantageous results are obtained when the dose is administered as a divided dose, producing a high plasma level followed by a drop in level and then a high level again. Thus, the use of substantially 800 mg/m$^2$ for the total of the constituent doses of a divided dose should be mentioned.

Compounds suitable for use according to the present invention are those of the general formula

ArCONH(CH$_2$)$_n$Y  (I)

in which

Ar represents an unsubstituted or substituted ring system comprising two or more fused aromatic rings and having an aromatic nitrogen atom or an oxygen atom peri to the carboxamide side chain, Y represents C(NH)NH$_2$, NHC(NH)NH$_2$ or NR$_4$R$_5$, where each of R$_4$ and R$_5$ separately is H or lower alkyl optionally substituted by one or more of the same or different substituents selected from hydroxy, lower alkoxy and amino functions, or R$_4$ and R$_5$ together with the nitrogen atom to which they are attached form a 5- or 6-membered heterocyclic ring optionally containing a further hetero atom; and n represents an integer from 2 to 6, and their physiologically tolerable acid addition salts and N-oxides thereof.

The ring system may comprise, for example, three fused aromatic rings, preferably linear, or two fused aromatic rings with a carbocyclic or heterocyclic aromatic ring as substituent. Of the fused aromatic rings, one or more may be heterocyclic.

In a preferred embodiment of the present invention there is used a compound of the general formula

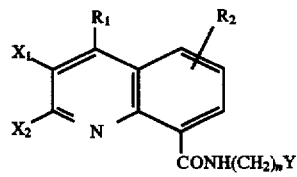

in which

R$_1$ represents H, CH$_3$ or NHR$_o$, where R$_o$ is H, COCH$_3$, SO$_2$CH$_3$, COPh, SO$_2$Ph or lower alkyl optionally substituted with hydroxy, lower alkoxy and/or amino functions;

R$_2$ represents H or lower alkyl, halogen, CF$_3$, CN, SO$_2$CH$_3$, NO$_2$, OH, NH$_2$, NHSO$_2$R$_3$, NHCOR$_3$, NHCOOR$_3$, OR$_3$, SR$_3$, NHR$_3$ or NR$_3$R$_3$ (where R$_3$ is lower alkyl optionally substituted with hydroxy, lower alkoxy and/or amino functions), and/or may represent the substitution of an aza (—N=) group for one of the methine (—CH=) groups in the carbocyclic ring, Y represents C(NH)NH$_2$, NHC(NH)NH$_2$ or NR$_4$R$_5$, where each of R$_4$ and R$_5$ separately is H or lower alkyl optionally substituted with hydroxy, lower alkoxy and/ or amino functions, or R$_4$ and R$_5$ together with the nitrogen atom to which they are attached form a 5- or 6-membered heterocyclic ring optionally containing a further hetero atom;

n represents an integer from 2 to 6;

$X_1$ represents H, and $X_2$ represents a phenyl or pyridyl ring unsubstituted or substituted by a substituent $R_6$, or $X_1$ and $X_2$, together with the carbon atoms to which they are attached, form a fused benzene ring unsubstituted or substituted by a substituent $R_6$, and $R_6$ represents lower alkyl, halogen, $CF_3$, CN, $SO_2CH_3$, $NO_2$, OH, $NH_2$, $NHSO_2R_3$, $NHCOR_3$, $NHCOOR_3$, $OR_3$, $SR_3$, $NHR_3$ or $NR_3R_3$ (where $R_3$ is lower alkyl optionally substituted with hydroxy, lower alkoxy and/or amino functions); or a phenyl ring optionally further substituted by lower alkyl, halogen, $CF_3$, CN, $SO_2CH_3$, $NO_2$, OH, $NH_2$, $NHCOR_3$, $NHCOOR_3$, $OR_3$, $SR_3$, $NHR_3$ or $NR_3R_3$ (where $R_3$ is lower alkyl optionally substituted with hydroxy, lower alkoxy and/or amino functions); and/or may represent the substitution of an aza (—N=) group for one of the methine (—CH=) groups in the ring;

or a physiologically tolerable acid addition salt, or, especially when $X_1$=H and $X_2$ is unsubstituted or substituted phenyl or pyridyl, a 1-N-oxide thereof.

A compound of the general formula Ia in which $X_1$ and $X_2$ complete a fused ring and $R_1$ represents an unsubstituted or substituted phenyl group should also be mentioned.

Another class of compounds is, for example, represented by the general formula Ib

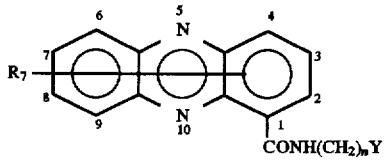

Ib in which $R_7$ represents H or up to three substituents, at positions selected from 2 to 4 and 6 to 9, wherein any two or all of the substituents may be the same or different and the substituents are selected from lower alkyl radicals; lower alkyl radicals substituted by one or more of the same or different substituents selected from hydroxy, lower alkoxy and/or amino functions; OH; SH; $OCH_2Ph$; OPh; $NO_2$; halogen; $CF_3$; amino; $NHSO_2R_3$, $NHCOR_3$, $NHCOOR_3$, $OR_3$ and $SR_3$ (where $R_3$ has the meaning given above; and CONH $(CH_2)_n.Y'$ (where n' and Y' are as defined below), there being a maximum of one $CONH(CH_2)_n.Y'$ group; or any two of $R_7$ at adjacent positions represent —CH=CH—CH=CH— as part of an extra benzene ring or —O—$CH_2$—O— (methylenedioxy) and the third of $R_7$ has any one of the meanings given above with the exception of an OH at position 2;

Y and Y', which may be the same or different, each has the meaning given above for Y; and n and n', which may be the same or different, each has the meaning given above for n;

and physiologically tolerable acid addition salts, 5- and 10-mono-N-oxides and 5,10-di-N-oxides thereof.

These compounds may be prepared by methods known per se, for example by methods described in EP 98098 A, in EP 206802 A and in EP 172744 A or by analogous methods.

When used herein, the term "lower alkyl" denotes an alkyl group having from 1 to 5, preferably 1 to 4, carbon atoms.

An amino function as substituent of a lower alkyl radical represented by any of $R_3$, $R_4$, $R_5$, $R_o$ and $R_7$ may be unsubstituted or, for example, substituted by one or two lower alkyl groups (where lower alkyl has the meaning given above), especially by one or two methyl groups. Thus, for example, an amino substituent of a lower alkyl radical represented by $R_3$, $R_4$, $R_5$, $R_o$ and/or $R_7$ may be $NH_2$, $NHCH_3$ or $N(CH_3)_2$.

A lower alkoxy group as substituent of a lower alkyl radical represented by $R_3$, $R_4$, $R_5$, $R_o$ and/or $R_7$ is especially a methoxy group.

A heterocyclic radical represented by $R_4$ and $R_5$ and the nitrogen atoms to which they are attached may, if desired, contain an additional hetero atom, and is 5- or 6-membered. An example is a morpholino group.

Examples of optionally substituted lower alkyl groups include those substituted by hydroxy, lower alkoxy or an amino function, for example lower alkyl optionally substituted with hydroxy, amino, methylamino, dimethylamino or methoxy. when $X_1+X_2$ complete a fused benzene ring such lower alkyl groups are preferably unsubstituted or substituted with hydroxy and/or amino groups.

In a $NR_3R_3$ group the two $R_3$ substituents may be the same or different, but are preferably the same.

A preferred class of compound of the above formula I where $X_1$ represents H and $X_2$ represents a phenyl or pyridyl ring is where $R_1$ represents H, and, more especially, $R_2$ represents H, Y represents $N(CH_3)_2$, n represents 2 and if $X_2$ represents a pyridyl ring, that ring is unsubstituted, and if $X_2$ represents a phenyl ring that ring is unsubstituted or substituted by halogen, $NO_2$ or $OCH_3$.

A pyridyl ring represented by $X_2$ is preferably a 4-pyridyl ring.

The use of an acridine carboxamide of the general formula

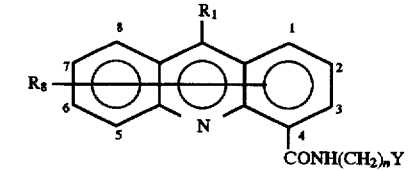

I' where $R_1$ and n have the meanings given above, $R_8$ represents H or up to two of the groups $CH_3$, $OCH_3$, halogen, $CF_3$, $NO_2$, $NH_2$, $NHCOCH_3$, and $NHCOOCH_3$ placed at positions 1-3 and 5-8, and/or may represent the substitution of an aza (—N=) group for one of the methine (—CH=) groups in the carbocyclic ring;

and

Y represents $C(NH)NH_2$, $NHC(NH)NH_2$, or $NR_4R_5$, where each of $R_4$ and $R_5$ is H or lower alkyl optionally substituted with hydroxyl and/or amino groups;

and where any lower alkyl radical has up to 4 carbon atoms, and the physiologically tolerable acid addition salts thereof, should especially be mentioned.

A preferred subclass of these compounds of formula I' are those where $R_1$ represents H or $NH_2$, $R_8$ represents up to two of 1-, 5-, 6-, 7- and 8-$NO_2$, 5- and 6-$CH_3$, and 5-Cl, Y represents $NHC(NH)NH_2$, $N(CH_3)_2$, or $NHCH_2CH_2OH$, and n represents 2.

Compounds specifically identified in EP 98098 A, EP 206802 A and EP 172744 A and in the literature references given above should also be mentioned.

When any of $R_2$, $R_6$ and $R_8$ represents the substitution in the ring of an aza group for one of the methine groups, that ring may be unsubstituted or substituted as specified above.

Compounds of the general formula Ia or I' in which $R_6$ or $R_8$ represents the substitution of an aza group for one of the methine groups and which optionally contains a further $R_6$ or $R_8$ substituent(s) are novel, and as such form part of the present invention.

The compounds used according to the invention, including compounds of formulae Ia and Ib, form pharmaceutically acceptable addition salts with both organic and inorganic acids. Examples of suitable acids for salt formation are hydrochloric, sulphuric, phosphoric, acetic, citric, oxalic, malonic, salicylic, malic, fumaric, succinic, ascorbic, maleic and methanesulphonic acids.

When used as a means of circumventing mdr, in combination with another cytotoxic drug, for example a DNA-reactive agent, a DNA-synthesis inhibitor or an agent which disrupts the mitotic apparatus, the compound of the general formula I may be administered together with, before or after the other cytotoxic drug. DACA could be given, for example, up to ±2 days of a second drug, or alternatively could be given as a separate or alternating course with another cytotoxic drug and separated by a period of bone marrow or other host tissue recovery, generally 3 to 4 weeks. DACA may, for example, be administered by intravenous infusion using the divided dose regime mentioned above, for example as a series of 2 to 4 administrations over a period of 2 to 4 hours.

Suitable DNA-reactive agents are, for example, cisplatin, cyclophosphamide, bleomycin and carboplatin. Suitable DNA synthesis inhibitors are, for example, 5-fluorouracil, 5-fluorodeoxyuridine and methotrexate; and suitable agents that disrupt the mitotic apparatus are, for example, taxol and suitable Vinca alkaloids, for example, vincristine, vinblastine and vindesine. These agents should be used in a treatment schedule which has been found optimal for anti-tumour effect; for example, cyclophosphamide may be used at monthly intervals, and vincristine at monthly or weekly intervals.

There are four main types of multidrug resistance related to topo II inhibitor:

(a) No change in the topoisomerase enzyme but increased transport of the drug out of the cell. DACA is not susceptible to this, while etoposide and doxorubicin are.

(b) No change in the enzyme, but an increase in drug detoxifying enzymes. This applies to doxorubicin but not to etoposide or DACA.

(c) A quantitative change (decrease) in the amount of topoisomerase II enzyme. DACA, etoposide and doxorubicin are equally susceptible, since DNA damage depends on the amount of enzyme present. Since the amount of topo II is regulated during the cell division cycle, cytokinetic resistance, whereby non-cycling cells resist the effects of topo II agents, may involve this type of resistance.

(d) A qualitative change in the topoisomerase enzyme, a result either of a switch in gene expression (there are two genes for topoisomerase II and one is normally dominant) or of a mutation in the gene, or of a change in modification of the enzyme after it has been synthesised. This results in a change in drug-target interaction. The qualitative change is accompanied by a differential change in sensitivity: in general, cells become highly resistant to amsacrine, moderately resistant to etoposide and doxorubicin, and, we have ascertained, minimally resistant to DACA.

Investigation of the cytotoxicity of DACA under conditions of continuous drug exposure in a variety of human and mouse cell lines and in a panel of 60 human cell lines revealed $IC_{50}$ values (defined as drug concentration required over approx. 5 cell doubling times for the reduction of the final cell culture density by 50%) ranging from 0.09 µM to 3.4 µM, and a mean $IC_{50}$ value for human cell lines of 1.3 µM. The latter value compared with 2 µM for the 4-pyridyl quinoline analogue, 0.76 µM for amsacrine, 0.1 µM for the amsacrine analogue 4'-(9-[4-[N-methylcarboxamido]-5-methyl]-acridinylamino)methanesulphon-m-anisidide ("CI-921") and 81 µM for etoposide. Whereas the patterns of cytotoxicity of amsacrine, CI-921 and etoposide in the human cell line panel were very similar, those of DACA and its pyridoquinoline analogue were quite different, suggesting differences in mode of action.

A multidrug resistant subline of P388 murine leukaemia (P/ACTD) was tested for sensitivity to DACA. This line was cross-resistant to actinomycin D, doxorubicin, mitoxantrone, etoposide and vincristine. Its resistance to vincristine was overcome by the presence of verapamil (10 µM). It stained for the presence of P-glycoprotein, consistent with the presence of transport-mediated multidrug resistance. This line was sensitive to DACA in vitro and in vivo, suggesting that DACA may be useful in at least some types of multidrug resistance.

DACA was also able to overcome, to a large extent, other mechanisms of multidrug resistance, as demonstrated in a series of sublines of Jurkat leukaemia cells which were highly resistant to amsacrine, etoposide and doxorubicin. Two of these lines had been selected for resistance to amsacrine, and were more than 100-fold cross-resistant to amsacrine but only 2- to 4-fold cross-resistant to DACA. These lines exhibited resistance mechanisms which were distinguishable from transport-mediated multidrug resistance. We believe that this ability to overcome resistance mechanisms accounts for the different $IC_{50}$ patterns observed with the human cell line panels.

It is apparent that in many tumours, regrowth during therapy is associated with resistance. The type of resistance is not yet properly characterised, but if it involves the mechanisms discussed above, DACA may be useful for second time treatment, especially in the divided dose regime mentioned above.

The use of the above compounds and combinations in the treatment of sarcoma and of lung, breast, ovarian and testicular cancer should especially be mentioned.

The use of compounds of the general formula I to treat colon tumours has been suggested previously, but there has been no evidence of their suitability for this treatment and there has been no indication that they are effective in test systems even with delay of initiation of treatment beyond day 2 or 3 after tumour implantation, as is usual in tests. There has also been no disclosure of high activity against such tumours. Such high activity would not have been expected since the most closely structurally related topo II inhibitor, amsacrine, is inactive.

An initial experiment against advanced colon 38 tumour (on day 11 after implantation), using the same schedule of administration as used for Lewis lung (3 injections at 4-day intervals) gave only a modest growth delay (4 days).

However, by adjustment of the administration schedule of DACA, growth delay of the advanced colon 38 tumour (5–8 mm in diameter) was increased to more than 21 days. Thus, while intermittent schedules (270 mg/kg $q^4$ days×3; 400 mg/kg $q^7$ days×3) provided only modest growth delays (3 days and 7 days, respectively), repeated injection schedules (4 injections at 30 minute intervals; 180+120+120+120 µmol/kg, q⁷ days×3) provided a 21 day growth delay. Such results were completely unexpected.

We have found that a low drug concentration for a long time (for example 6 hours) is much more toxic than a high concentration for a correspondingly shorter time. We believe these unusual "self-inhibitory" properties of DACA may be of help in the new divided dose administration strategy. Because DACA diffuses more slowly in solid tumours such as colon tumours, than in normal tissues, peak drug concentrations in tumours are lower than in normal tissues: an obvious disadvantage. However, because, as we have found, higher concentrations of DACA are less inhibitory than lower ones., the adjustment of the dosing strategy may provide partial protection of normal tissues.

DACA or other compound of the general formula I may be administered, for example, in a divided dose over a period of up to 4 hours, for example 2 to 4 hours, followed by a rest, for example for 3 to 4 weeks. The dose may be divided into two to four administrations over the 2 to 4 hour or other administration period, and the first dose may be larger than the others, that is, as a loading dose; administrations may be given intravenously. For example, a short-term intravenous infusion of 10 to 30 minutes (for example 15 minutes) may be used, followed by a further such infusion after, for example, 1 hour. This schedule differs from that normally used for other cytotoxic agents, which involves periods of intravenous infusion administered daily, for example for 3 to 7 days, or long-term intravenous infusion over a number of days, for example for a week.

We have found that DACA also has activity against melanoma cell lines and human tumour xenografts of these lines, and it is believed that this activity is improved by the same strategy.

The cytotoxicity of DACA was assessed in a panel of primary human melanoma cultures derived from fresh surgical melanoma specimens. $IC_{50}$ values ranged from 0.2 o 1.5 µM, and a feature of the data was the ability of DACA to kill much higher proportions of cells (>99%) in some cultures, as compared to a maximum of 90% for etoposide.

A further experiment was carried out using human melanoma line, implanted subcutaneously in nude (athymic) mice. Treatment was started when the tumours were 4–7 mm in diameter. DACA was administered ip as a divided dose (2×100 mg/kg body weight at 0 and 60 min) and a second similar administration (2×100 mg/kg) was given after 7 days. A growth delay of 30 days was obtained.

The positive results achieved by DACA in these treatments is surprising since melanoma is more difficult to treat with chemotherapy than are other forms of tumour.

Moreover, Berger et al. (Berger D. P., Winterhalter B. R., Flebig H. H., "Conventional chemotherapy" in "The Nude Mouse in Oncology Research", 1st ed. London: CRC Press, 1991, 165–84, ed. Boven and Winograd) states that melanoma xenografts are resistant to treatment by doxorubicin and etoposide, so activity by a drug in this class is completely unexpected. A summary of the activity of various other agents against subcutaneous melanoma xenografts growing in nude mice is given by Berger et al. as follows:

| Drug | Percentage of xenografts responding |
|---|---|
| Topo II inhibitors | |
| Doxorubicin | 5% (total of 5 studies) |
| Etoposide | 0% (2 studies) |
| Other drugs | |
| Bleomycin | 0% |
| Cisplatin | 13% |
| Cyclophosphamide | 11% |
| Dacarbazine | 17% |
| 5-Fluorouracil | 14% |
| Methotrexate | 7% |
| Mitomycin C | 32% |
| Vinblastine | 10% |
| Vincristine | 43% |

In pharmacokinetic studies using radioactive (tritium-labelled) DACA high levels of active ingredient have been found in all tissues, including brain, with a long elimination $t_{1/2}$ of 37–176 h. As determined by HPLC, the tissue concentrations of DACA 1 h after intraperitoneal administration of drug (400 µmol/kg) were 45, 185, 139, and 57 µmol/kg in brain, liver, kidney and heart, respectively. The corresponding AUC values (AUC=area under the plasma concentration-time curve) were 218, 547, 492 and 147 µmol.h/l , respectively, as compared to the plasma AUC of 26.6 µmol.h/l. DACA showed relatively high rates of passage across the blood brain barrier. We believe that administration of DACA, especially at the new divided dose-high constituent dose frequency regime mentioned above, will be helpful in combating brain tumours. With the exception of nitrosoureas, few of the antitumour agents currently in use possess the physicochemical properties required for adequate penetration of the blood-brain barrier (Greig M. H. (1987), Cancer Treat. Rep. 11: 157).

We also propose the use of DACA and related compounds with a "rescue" treatment with a second drug which by itself is not an active agent but which displaces DACA or the other compound from the DNA. This DNA-binder, or chemoprotector, should have a lower intrinsic toxicity and less efficient tissue distribution properties than the cytotoxic agent, thus sparing rapidly growing and highly vascularised normal tissues such as bone marrow from cytotoxic effects. Use of the new schedule of administration of DACA or other compound of the general formula I or a physiologically tolerable acid addition salt or 1-N-oxide thereof, combined with "rescue" treatment with a chemoprotector, should especially be mentioned. Timing of administration of the chemoprotector will depend on the pharmacokinetics of DACA or other drug used. The chemoprotector may, for example, be administered at the same time as or up to 30 minutes after one or more of the constituent doses of a divided dose of that drug; by such means doses of, for example, 200 mg/kg or even 300 mg/kg of DACA—doses which are normally toxic—may be possible.

The following Examples illustrate the invention.

EXAMPLES

EXAMPLE 1

Activity of DACA against cultured multidrug resistant human leukaemia cells

Materials and Methods

Acridine carboxamide hydrochloride, synthesised in the Cancer Research Laboratory (Atwell G. J., et al., J. Med. Chem. 1987, 30, 664–669), and amsacrine isethionate, obtained from the Parke-Davis Division of the Warner-Lambert Company, Ann Arbor, USA, were dissolved in 50% v/v aqueous ethanol to make stock solutions of 2–5 mmol/l and stored at −20° C. Other cytotoxic drugs were available either from the NCI repository (Monks A., et al., J. Natl. Cancer Inst. 1991, 83, 757–766) or were obtained as described in Marshall E. S., et al., J. Natl. Cancer Inst. 1992, 84, 341–344 and Finlay, et al., Eur. J. Cancer Clin. Oncol. 1986, 22, 655–662. Cell lines were from the NCI repository except for MM-96 (Dr. R. Whitehead, Ludwig Institute, Melbourne, Australia), FME (Dr. K. M. Tveit, Norwegian Radium Hospital, Oslo, Norway) and Jurkat normal and multidrug-resistant lines (Dr. K. Snow and Dr. W. Judd, Department of Cellular and Molecular Biology, University of Auckland). Melanoma tissue was obtained from patients with pathologically confirmed metastatic and recurrent melanomas under Auckland Hospital Ethical Committee guidelines. Cells were released by digestion of tissue (at 50 mg.ml$^{-1}$) with collagenase (1 mg.ml$^{-1}$) and DNAase (50 µg.ml$^{-1}$) with continuous stirring at 37° C. for 1 to 2 hours, and cultured as previously described (Marshall E. S., et al., J. Natl. Cancer Inst. 1992, 84, 341–344).

Tumour cell lines were cultured in 96-well plates. Growth of NCI cell lines was assessed using sulphorhodamine B staining (Skehan P., et al., J. Natl. Cancer Inst. 1990, 82, 1107–1112), that of the leukaemia lines with (4,5-dimethylthiazole-2-yl)-2,5-diphenyltetrazolium (MTT) staining (Mosmann T., J. Immun. Methods 1983, 65, 55–63) and that of the primary human tumour material by $^3$H-thymidine incorporation (Marshall E. S., et al., J. Natl. Cancer Inst. 1992, 84, 341–344). Primary tumour material was cultured in 96-well plates in which the wells were coated with agarose to inhibit selectively the growth of normal cells. (Marshall E. S., et al., J. Natl. Cancer Inst. 1992, 84, 341–344). Primary cultures were incubated at 37° C. in sealed perspex boxes containing a humidified atmosphere of 5% $CO_2$ and 5% $O_2$ in nitrogen for 7 days. 5-Methyl-[$^3$H]-thymidine (20 Ci.mmol$^{-1}$; 0.04 µCi per well), thymidine and 5-fluorodeoxyuridine (each at final concentrations of 0.5 µM) were added in medium to cultures (20 µl per well) 24 h before terminating the cultures. Cells were aspirated on to glass fibre filters using a multiple automated sample harvester (LKB Wallac OY Beta Harvester). The filter discs were washed for 15 seconds with water, dried, and the amount of tritium retained quantified by liquid scintillation.

$IC_{50}$ values were defined as in Paull K. D., et al., J. Natl. Cancer Inst. 1989, 81:1088–1092, where growth, as indicated by staining or thymidine incorporation, corresponded to 50% of that of the control cultures. DELTA values were determined for groups of logarithmic $IC_{50}$ values as deviations from the mean, with positive DELTA values representing higher drug sensitivity relative to the mean. Variances of DELTA values were expressed as standard deviations in $log_{10}$ units. Comparison of DELTA values was made using Pearson correlation coefficients. Resistance factors were defined as the ratios of $IC_{50}$ values between the resistant line and the parent line. Statistical evaluation was performed either with NCI programmes, with RS/1 software (BBN Research Systems, Cambridge, Mass., USA), or with Sigmaplot (Jandel Scientific, San Rafael, Calif., USA).

Results

The effect of DACA on the growth of cultured cells was assessed by continuous drug exposure. DACA inhibited the growth of two human Jurkat T cell leukaemia lines, one diploid (L) and the other tetraploid (B1), with $IC_{50}$ values each of 380 nM. These values were similar to those of other human leukaemia cell lines, which ranged from 290 to 760 nM (CEM-CCRF, 410 nM; MOLT-4, 290 nM; Daudi, 400 nM; Raji, 370 nM, U937, 590 nM; HL-60, 620 nM; K-562, 760 nM). Four multidrug-resistant cell lines, developed from JL and JB1 by in vitro exposure to increasing concentrations of doxorubicin ($L_D$ and $B1_D$) or amsacrine ($L_A$ and $B1_A$) (Finlay G. J., et al., J. Natl. Cancer Inst. 1990, 82, 662–667, Snow K., et al., Br. J. Cancer 1991, 63, 17–28) were tested.

DACA was compared with six other drugs including four topo II poisons, doxorubicin, mitozantrone, etoposide and amsacrine. Resistance factors for the topo II poisons were consistently higher than those for DACA (Table 1). In contrast, the topoisomerase I poison camptothecin showed no cross resistance, and the mitotic inhibitor vincristine showed a different pattern of resistance with the $B1_D$ line having the highest resistance (Table 1).

TABLE 1

Drug-resistant Jurkat Leukaemia sublines.
Resistance factors

| | doxo-rubicin | mitoxan-trone | etopo-side | amsa-crine | DACA | campto-thecin | vincris-tine |
|---|---|---|---|---|---|---|---|
| $L_A$ | 3.8 | 42 | 11 | 130 | 2.0 | 1.0 | 1.5 |
| $L_D$ | 16 | 160 | 93 | 110 | 2.5 | 0.97 | 3.6 |
| $B1_A$ | 11 | 59 | 22 | 240 | 3.9 | 0.48 | 2.0 |
| $B1_D$ | 15 | 8.4 | 83 | 8.8 | 1.9 | 0.86 | 10 |

One method of providing a visual comparison of the patterns of resistance is to plot DELTA values (Paull K. D., et al., J. Natl. Cancer Inst. 1989, 81, 1088–1092) where the differences in bar lengths are used as a measure of relative resistance. FIG. 1 shows a comparison of DELTA values in log mean graph format for DACA, amsacrine, etoposide, doxorubicin, vincristine, 5-fluorouracil, camptothecin and mitozantrone for the panel of multidrug resistant Jurkat leukaemia lines using MTT staining; JL/AMSA and JB/AMSA were selected for resistance to amsacrine and JL/DOX and JB/DOX were resistant to doxorubicin. DACA clearly shows a pattern distinct from doxorubicin.

Figure 2:
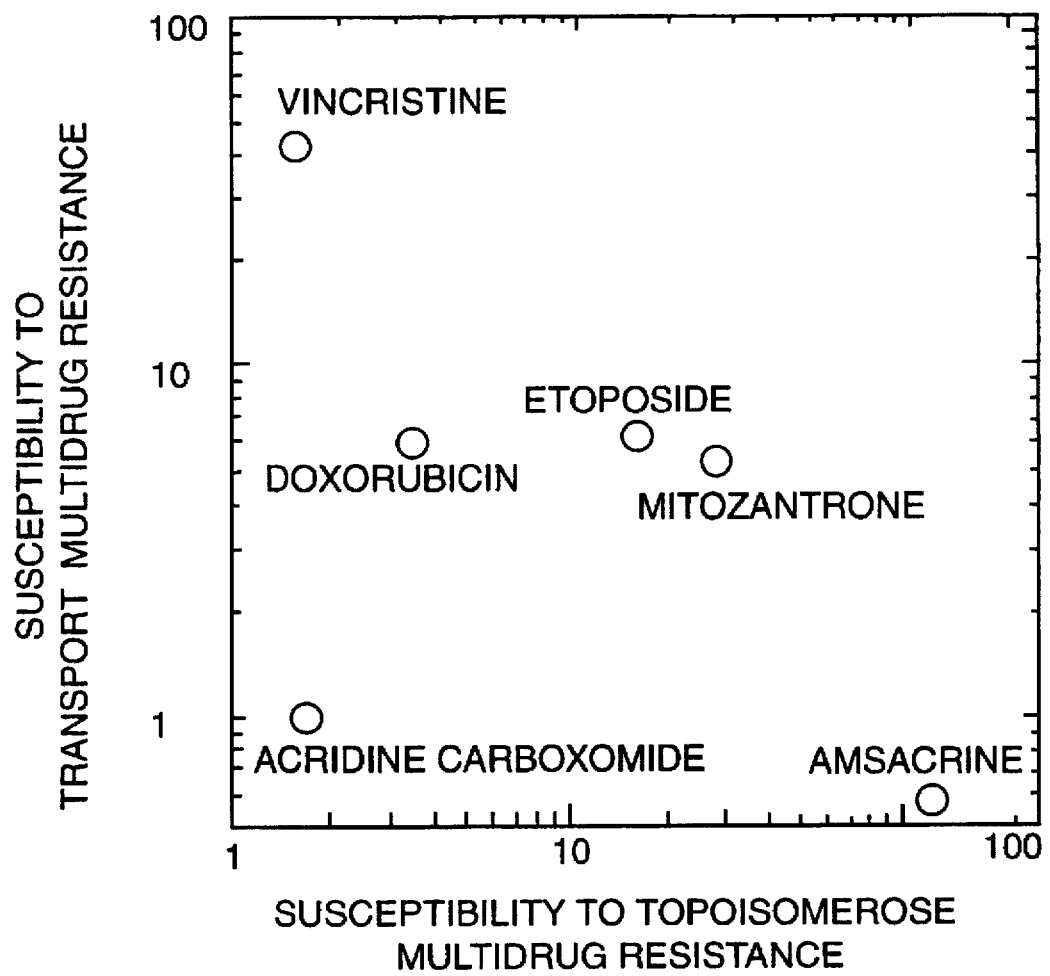
FIG. 2 is a scattergram showing the transport multidrug resistance against the susceptibility to topoisomerase multidrug resistance for the same 6 drugs of FIG. 1.

A second method of comparing agents is to plot resistance factors for one of the lines against another. Since the Jurkat lines exhibited predominantly "altered topoisomerase" resistance (Finlay G. J., et al., J. Natl. Cancer Inst. 1990, 82, 662–667, Sugimoto Y., et al., Cancer Res. 1990, 50, 7962–7965), the resistance factors for one of these ($L_A$) was plotted versus the resistance factors for a P-glycoprotein positive multidrug resistant P388 Leukaemia line (P/DACT) which exhibits transport resistance (Baguley B. C., J. Natl. Cancer Inst. 1990, 82, 398–402). The results (FIG. 2) indicate that DACA is unique when compared to other topo II agents in that it is able to overcome two different multi-drug resistance mechanisms. Qualitatively similar graphs are obtained when the resistance factors of the other resistant Jurkat lines are plotted on the abscissa, or those from a P-glycoprotein positive, vinblastine resistant human leukaemia line ($CEM/VLB_{100}$) (Qian X., Beck W. T., Cancer Res. 1990, 50, 1132–1137) are plotted on the ordinate.

Figure 3A:
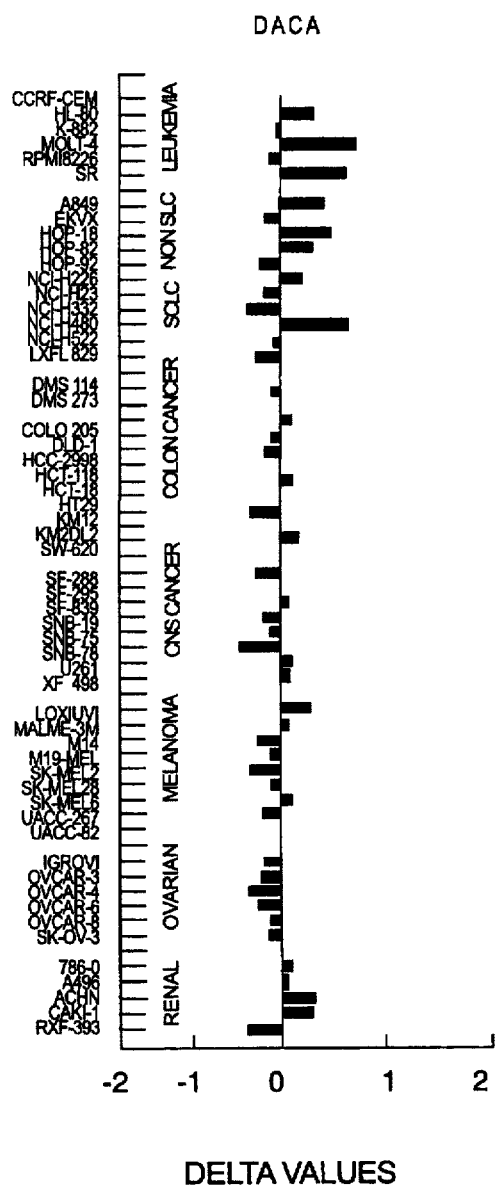
FIG. 3 is a plot of DELTA values of DACA compared with amsacrine, etoposide and doxorubin using protein staining.
Figure 3B:
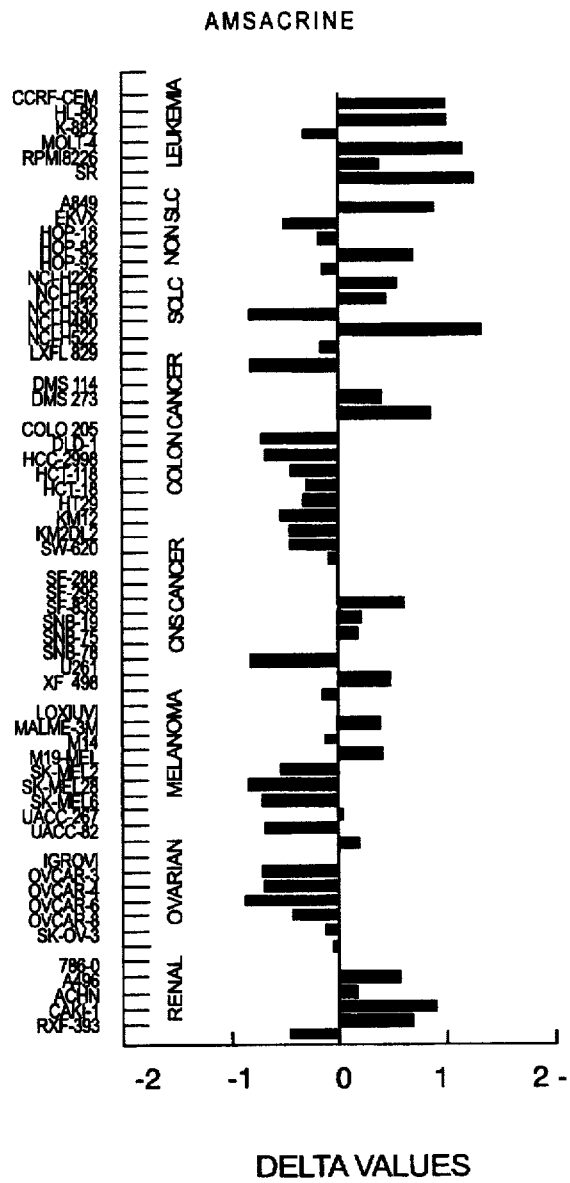
Figure 4A:
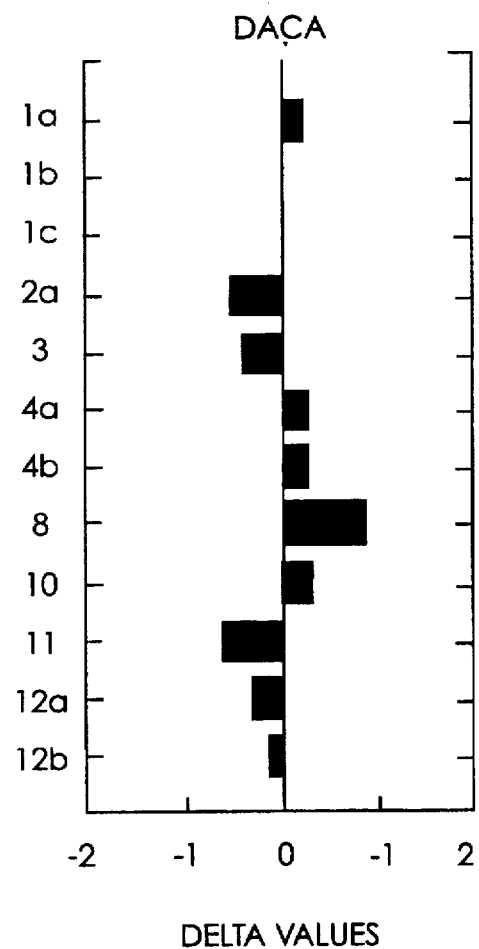
FIG. 4 is a plot of the DELTA values in a series of 12 primary melanoma cultures comparing DACA with the three other topo II agents as in FIG. 3.
Figure 4B:
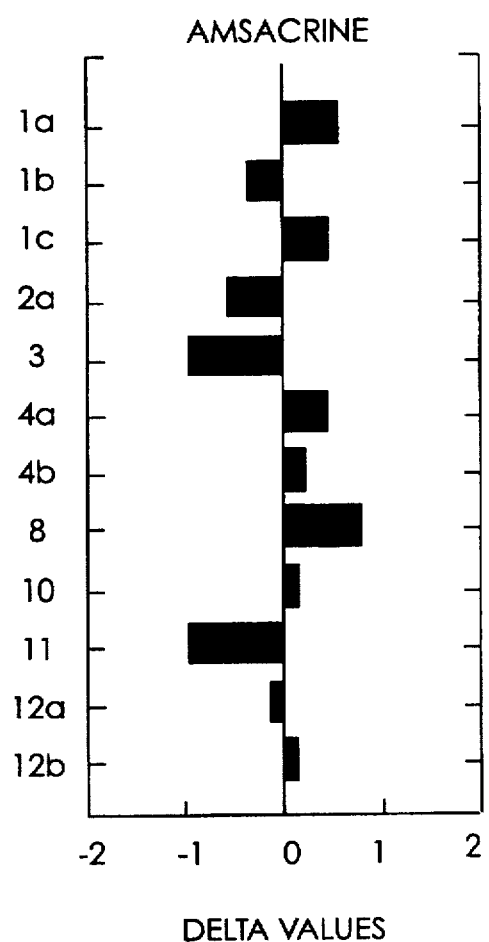
Figure 4C:
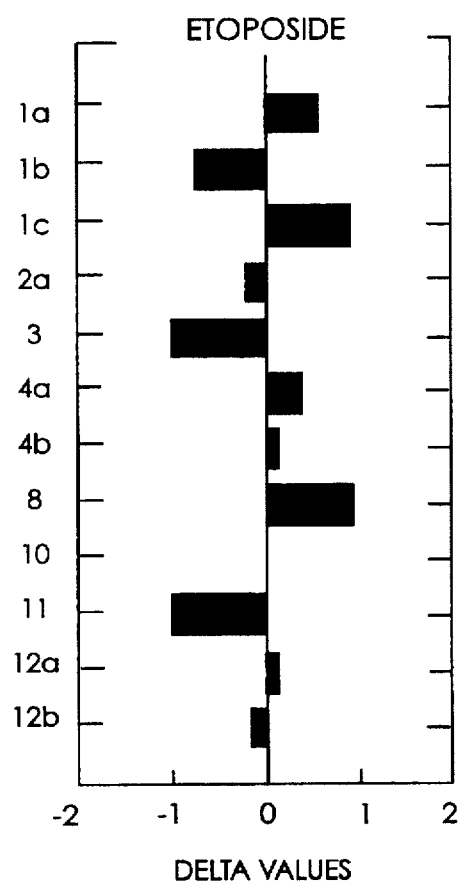
Figure 4D:
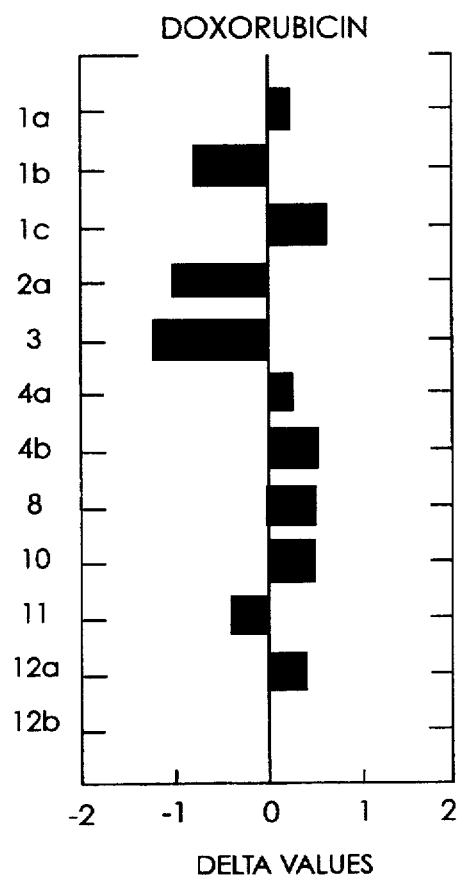

DACA was also compared with three other topo II agents using a panel of cell lines (data provided by Dr. Ken Paull from the National Cancer Institute, USA) encompassing a number of tumour types, and using protein staining. The mean $IC_{50}$ for DACA was 2,100 nM, as compared with amsacrine (520 nM), etoposide (21,000 nM) and doxorubicin (140 nM). The results, presented as DELTA plots, are compared with corresponding plots for three other topoisomerase II poisons in FIG. 3. The variance of DELTA values was considerably smaller for DACA (0.24 units) than it was for amsacrine (0.61 units) etoposide (0.55 units) or doxorubicin (0.44 units). The differences in DELTA values for amsacrine, etoposide and doxorubicin for primary human cultures imply that intrinsic resistance mechanisms exist and are partially overcome with DACA.

DACA was also compared in a series of 12 primary melanoma cultures. Tissue was excised from human malignant melanomas and cultured using a modified 96-well assay system in which the cells were cultured on agarose and assayed for proliferation using the $^3$H-thymidine incorporation assay as described in Marshall E. S., et al., J. Natl. Cancer Inst. 1992, 84, 341–344. The mean IC$_{50}$ for DACA was 590 nM, as compared with amsacrine (128 nM), etoposide (2,200 nM) and doxorubicin (56 nM). DELTA values for DACA, amsacrine, etoposide and doxorubicin are compared in FIG. 4. The variance of DELTA values was smaller for DACA (0.39 units) than for amsacrine (0.54 units), etoposide (0.66 units) or doxorubicin (0.63 units). The differences in DELTA values for amsacrine, etoposide and doxorubicin for primary human cultures again imply that intrinsic resistance mechanisms exist and are partially overcome with DACA.

EXAMPLE 2

Activity of DACA against advanced colon 38 and melanoma in mice

Materials and Methods

Colon 38 carcinoma was obtained from the Mason Research Institute (Worchester, Mass., USA) and was grown in BDF$_1$ hosts. Tumour fragments (1 mm$^3$) were implanted subcutaneously in anaesthetised mice. Tumours had grown to the appropriate size 9 days after implantation. A melanoma tumour line (WADH) was developed in the Cancer Research Laboratory. Tumour cells were grown in culture and 1×10$^6$ cells were implanted intradermally into the flank of nude (C57BI/J genetic background) mice. Mice were grown under sterile surroundings until tumours were of appropriate size.

Tumours were measured 3× (colon 38) or 2× (xeno-graft) weekly with callipers and tumour volumes calculated as 0.52a$^2$b, where a and b were the minor and major tumour axes. Tumour growth delays were measured at a time when tumour volumes of treated and control animals had increased by 4-fold.

Results

Figure 5:
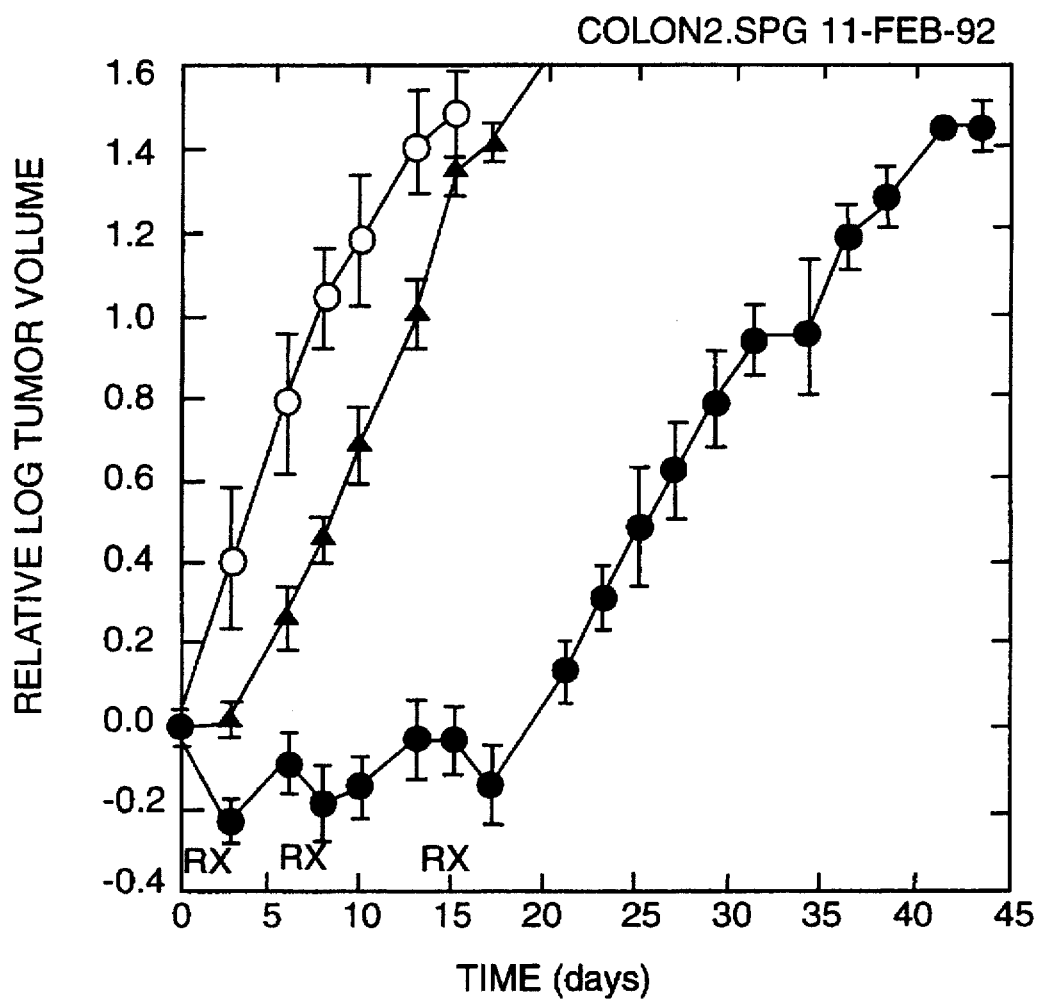
FIG. 5 is a graph showing a single maximum tolerated dose of DACA versus four injections at 30 minute intervals comparing relative tumor volume over time.

The effect of DACA on the growth of advanced colon 38 tumours in mice was investigated by implanting tumour fragments subcutaneously and allowing them to grow until they had reached a diameter of 5–8 mm. I.p. treatment of mice with a single maximum tolerated dose of DACA (150 mg/kg body weight), a treatment which was known to induce cures of intravenously implanted Lewis lung tumours (Finlay G. J., Baguley B. C., Eur. J. Cancer Clin. Oncol. 1989, 25, 271–277) caused only a slight growth delay (5 days; FIG. 5). However, when a divided dose (200 mg/kg) was administered over a period of 0.5–4 hours, greater delays were unexpectedly observed (Table 2). Repetition of these divided doses provided a substantial growth delay (23 days; FIG. 5) which was longer than that obtained with the maximum tolerated dose of amsacrine (2 days), cyclophosphamide (6.5 days) or 5-fluorouracil (13 days).

TABLE 2

Tumour growth delays (colon 38) treated with DACA

| Total dose | Schedule | Growth delay (days) |
|---|---|---|
| 100 | ip single dose (SD) | 4 |
| 150 | ip SD | 5 |
| 150 × 3 | ip SD every week × 3 | 7 |
| 150 | ip 2 doses, 0, 60 min | 5 |
| 200 | ip SD | toxic |
| 200 | ip 2 doses, 0, 30 min | 7 |
| 200 | ip 2 doses, 0, 60 min | 10, 12 (2 expts) |
| 200 | ip 2 doses, 0, 24 hours | 6 |
| 200 | ip 4 doses, 0, 30, 60, 90 min | 6 |
| 200 | iv 1 hour infusion | 7 |
| 200 | iv 3 hour infusion | 6.5 |
| 200 × 3 | ip (4 doses, 0, 30, 60, 90 min) × 3 | 23 |

Note: the 4 dose schedule was 65 + 45 + 45 + 45 mg/kg

Figure 6:
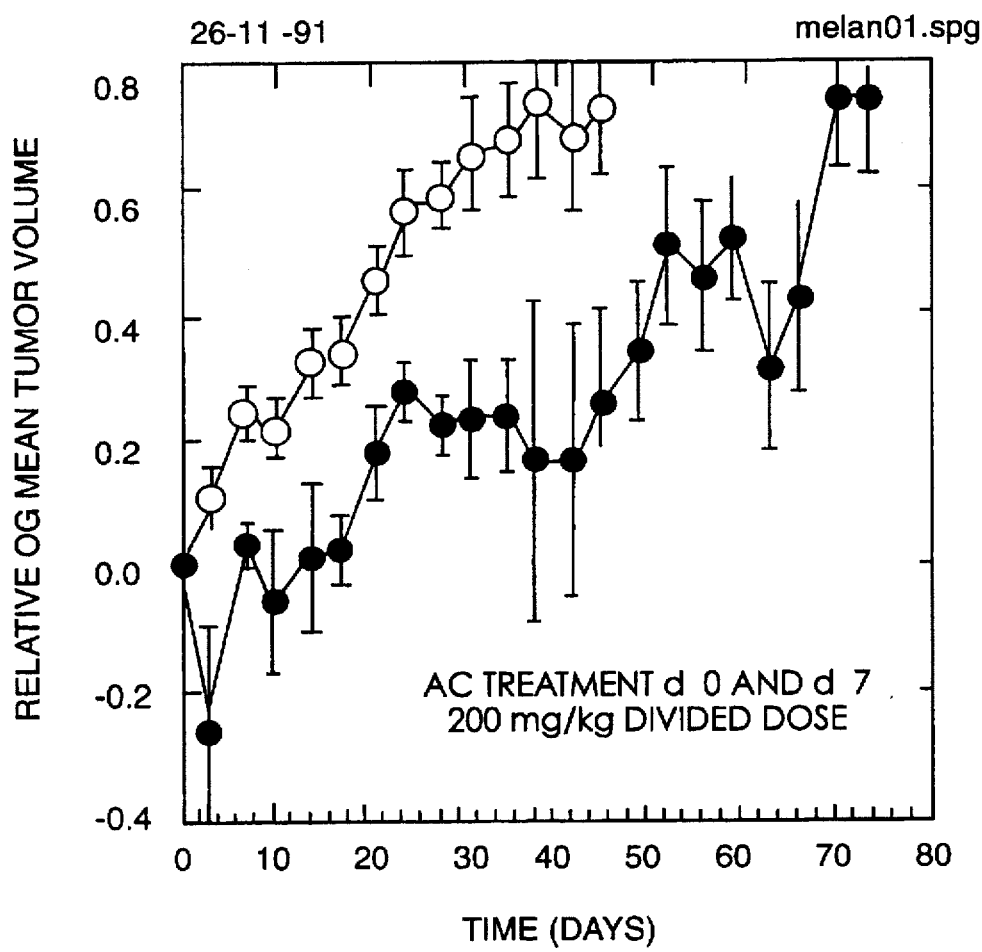
FIG. 6 is a graph showing DACA administered in divided doses at 0 and 7 days against controls comparing relative tumor volume versus treatment time in days.

A further experiment was carried out using human melanoma line, implanted subcutaneously in nude (athymic) mice using an inoculation of one million cells of a human melanoma cell line designated WADH. Treatment was started when the tumours were 4–7 mm in diameter. DACA was administered ip as a divided dose (2×100 mg/kg body weight at 0 and 60 min) and a second similar administration (2×100 mg/kg) was given after 7 days. A growth delay of 30 days was obtained (FIG. 6).

EXAMPLE 3

Exploitation of the self-inhibitory properties of a drug in the therapy of solid tumours One of the characteristics of solid tumours is that because of the poor vascularisation, oxygen, nutrients and chemotherapeutic drugs must diffuse for longer distances than they do in normal tissue (Wilson W. R., Denny W. A., Radiation Research: a Twentieth Century Perspective, 1st ed. v. 2. New York: Academic Press, 1992:796–801). In the case of anti-tumour agents, a gradient of drug concentration is established with the lowest drug concentration at greatest distances from the capillary. Since in all cases examined so far with existing clinical agents, cytotoxicity is related in a positive fashion to drug concentration, it follows that those areas most remote from the tumour blood supply are protected from drug cytotoxicity, a so-called "pharmacological sanctuary".

DACA is a DNA intercalating agent which acts on topo II and has the unusual property of inhibiting its own toxicity at concentrations above 5 μm. It also inhibits the formation of DNA-protein cross-links above 5 μM, consistent with the hypothesis that self-inhibition of DNA-protein cross-links is related to self-inhibition of toxicity. A simple model for this behaviour is that in order for topo II to form its complex with DNA (i.e. to form DNA-protein cross-links) it requires the presence of a DNA-drug complex (probability=p), surrounded on each side by drug-free DNA (probability=(1-p)). It follows that the probability of forming a productive complex is p(1-p)$^2$. When this function is plotted against experimental cytotoxicity data for DACA (Haldane A., et al., Cancer Chemother. Pharmacol. 1992, 29, 475–479), a good approximation is obtained (FIG. 7).

Figure 7:
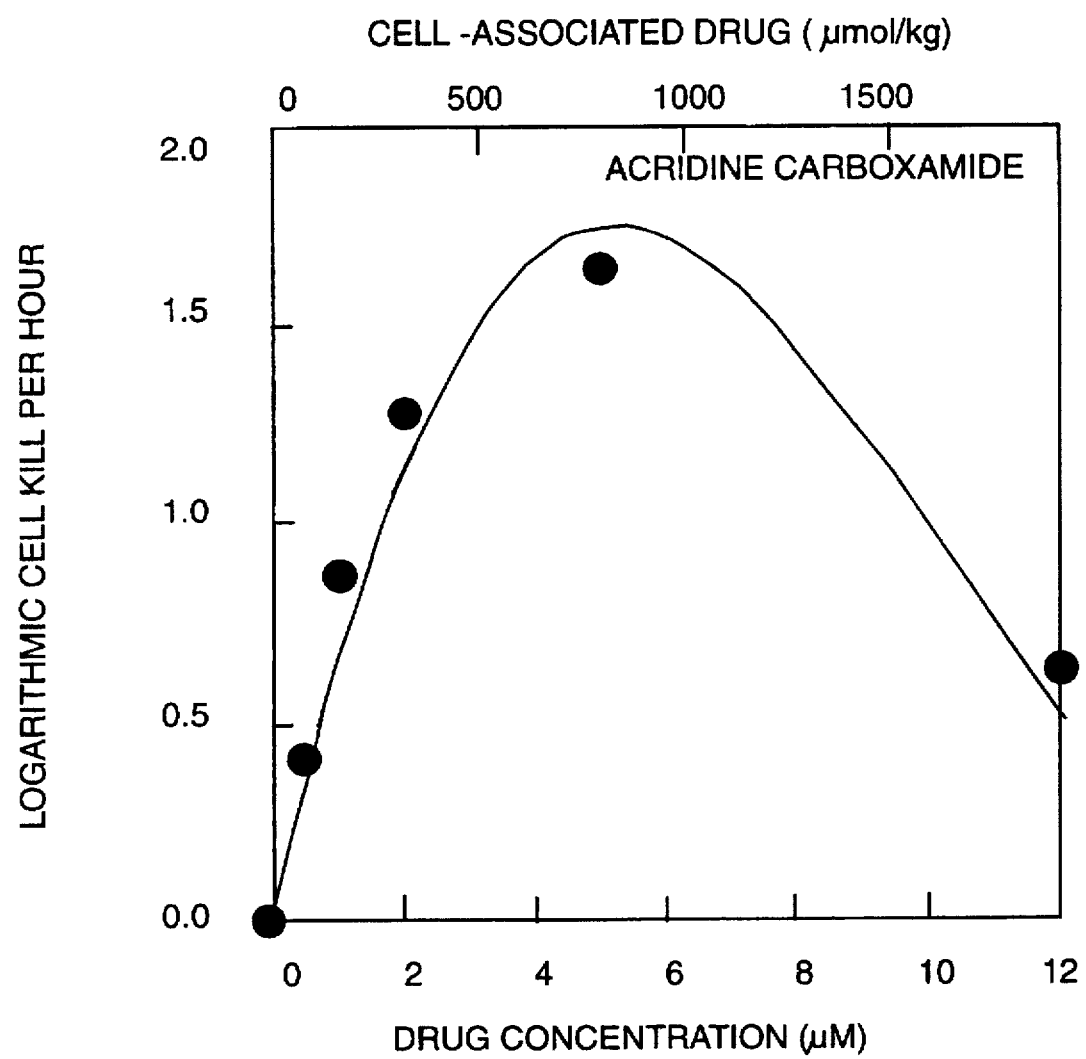
FIG. 7 is a graph showing toxicity versus cell-associated drug relating cell kill per hour against drug concentration comparing the experimental data with a theoretical model.

FIG. 7 can also be plotted as toxicity versus cell-associated drug (using unpublished data from the Cancer Research Laboratory which relates external drug concentration to cell-associated drug). It can be seen from FIG. 7 that if a tumour concentration gradient is established whereby the area of the tumour closest to the capillary has, for example, a concentration of 1800 μmol/kg, areas of the tumour which are more remote from the capillary, although having a lower drug concentration, will have higher cytotoxicity. Furthermore, host tissues, which have good blood supplies, will have high tissue drug concentrations and thus lower cytotoxicity. By this principle, DACA (and other compounds of this general class) could have a selectivity mechanism for solid tumours which is not possessed by other agents.

The practical application of this hypothetical situation requires that free drug plasma concentrations (and corresponding tissue concentrations of drug) fall into the range which will provide selectivity (i.e. greater than 1000 µmol/kg tissue). Preliminary results (Dr. James Paxton, personal communication) indicate that when DACA is administered at a maximally tolerated single drug dose (150 mg/kg body weight), drug concentrations in normal tissues (e.g. liver, spleen) slightly exceed 1000 µmol/kg. This principle may be exploited further by drug design or by combining DACA administration with that of a second chemoprotector agent which increases the self-inhibition of DACA (i.e. the descending part of the curve in FIG. 7) and thus lowers the average tissue drug concentration required for the application of this principle.

We claim:

1. A method for the treatment of advanced colon cancer, which method comprises administering to a patient in need thereof, by a divided dose schedule, a therapeutically effective amount of a compound which is an acridine carboxamide of formula I':

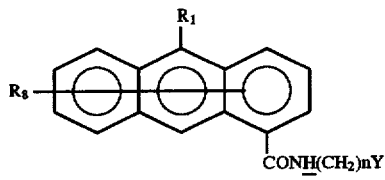

wherein $R_1$ is selected from the group consisting of H, $CH_3$ and $NHR_0$, wherein R0 is selected from the group consisting of H, $COCH_3$, $SO_2CH_3$, COPh, $SO_2Ph$ and $C_1$–$C_4$ alkyl which is unsubstituted or bears a substituent selected from the group consisting of hydroxy, $C_1$–$C_4$ alkoxy and amino;

n is an integer from 2 to 6;

$R_8$ is H or is one or two substituents selected from the group consisting of $CH_3$, $OCH_3$, halogen, $CF_3$, $NO_2$, $NH_2$, $NHCOCH_3$ and $NHCOOCH_3$ at positions 1–3 and 5–8; and Y is selected from the group consisting of $C(NH)NH_2$, $NHC(NH)NH_2$ and $NR_4R_5$ wherein each of $R_4$ and $R_5$ is H or $C_1$–$C_4$ alkyl unsubstituted or substituted by hydroxy or amino;

or a physiologically tolerable acid addition salt or N-oxide thereof; the divided dose schedule comprising a first administration and a second administration of the said compound wherein the second administration commences 15 minutes or more, but less than one day, after commencement of the first administration.

2. A method according to claim 1 wherein, in Formula I':

$R_1$ is H or $NH_2$ n is 2

$R_5$ is one or two substituents selected from the group consisting of 1-$NO_2$, 5-$NO_2$, 6-$NO_2$, 7-$NO_2$, 8-$NO_2$, 5-$CH_3$, 6-$CH_3$ and 5-Cl; and Y is selected from the group consisting of $NHC(NH)NH_2$, $N(CH_3)_2$ and $NHCH_2CH_2OH$.

3. A method according to claim 1 wherein the acridine carboxamide of formula (I') is N-[2-(dimethylamino)ethyl]acridine-4-carboxamide.

4. A method according to claim 1 wherein the compound is the dihydrochloride salt of N-[2-(dimethylamino)ethyl]acridine-4-carboxamide.

5. A method according to claim 1 which comprises administering, simultaneously or sequentially with the said compound, a second component selected from the group consisting of cisplatin, cyclophosphamide, bleomycin, carboplatin, 5-fluorouracil, 5-fluorodeoxyuridine, methotrexate, taxol, vincristine, vinblastine and vindesine.

6. A method according to claim 1 wherein the divided dose schedule comprises at least two administrations of drug over a period of up to 4 hours.

7. A pharmaceutical composition for use in the treatment of advanced colon cancer, comprising (i) a first component which is an acridine carboxamide of formula (I'):

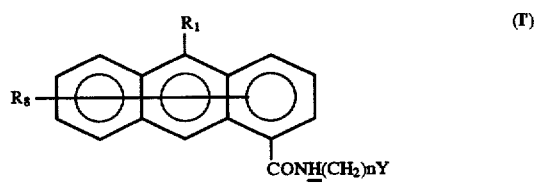

wherein $R_1$ is selected from the group consisting of H, $CH_3$ and $NHR_0$, wherein $R_0$ is selected from the group consisting of H, $COCH_3$, $SO_2CH_3$, COPh, $SO_2Ph$ and $C_1$–$C_4$ alkyl which is unsubstituted or bears a substituent selected from the group consisting of hydroxy, $C_1$–$C_4$ alkoxy and amino;

n is an integer from 2 to 6;

$R_8$ is H or is one or two substituents selected from the group consisting of $CH_3$, $OCH_3$, halogen, $CF_3$, $NO_2$, $NH_2$, $NHCOCH_3$ and $NHCOOCH_3$ at positions 1–3 and 5–8; and Y is selected from the group consisting of $C(NH)NH_2$, $NHC(NH)NH_2$ and $NR_4R_5$ wherein each of $R_4$ and $R_5$ is H or $C_1$–$C_4$ alkyl unsubstituted or substituted by hydroxy or amino;

or a physiologically tolerable acid addition salt or N-oxide thereof;

and (ii) a second component which is selected from the group consisting of cisplatin, cyclophosphamide, bleomycin, carboplatin, 5-fluorouracil, 5-fluorodeoxyuridine, methotrexate, taxol, vincristine, vinblastine and vindesine;

the said first and second components being present together in the same formulation.

8. A composition according to claim 7 wherein, in formula (I'), $R_1$ is H or $NH_2$ n is 2

$R_8$ is one or two substituents selected from the group consisting of 1-$NO_2$, 5-$NO_2$, 6-$NO_2$, 7-$NO_2$, 8-$NO_2$, 5-$CH_3$, 6-$CH_3$ and 5-Cl; and Y is selected from the group consisting of $NHC(NH)NH_2$, $N)CH_3)_2$ and $NHCH_2CH_2OH$.

9. A composition according to claim 7 wherein the derivative of formula (I') is N-[2-(dimethylamino)ethyl]acridine-4-carboxamide.

10. A composition according to claim 7 wherein the compound is the dihydrochloride salt of N-[2-(dimethylamino)ethyl]acridine-4-carboxamide.

11. A method according to claim 1 wherein the divided dose schedule comprises a third administration and optional further administrations of the said compound, the said third and optional further administrations each commencing 15 minutes of more, but less than one day, after commencement of the previous administration.

12. A method according to claim 1 wherein the divided dose schedule comprises at least 2 administrations of the said compound over a period of from 30 minutes to 4 hours.

13. A method according to claim 1 wherein the divided dose schedule comprises 2 to 4 administrations of the said compound over a period of 2 to 4 hours.

* * * * *